(12) United States Patent
Liversidge

(10) Patent No.: US 9,498,578 B2
(45) Date of Patent: *Nov. 22, 2016

(54) MEDICAL NEEDLE SAFETY DEVICES

(71) Applicant: Barry Peter Liversidge, Colchester (GB)

(72) Inventor: Barry Peter Liversidge, Colchester (GB)

( * ) Notice: Subject to any disclaimer, the term of this patent is extended or adjusted under 35 U.S.C. 154(b) by 742 days.

This patent is subject to a terminal disclaimer.

(21) Appl. No.: 13/706,776

(22) Filed: Dec. 6, 2012

(65) Prior Publication Data

US 2013/0116626 A1    May 9, 2013

Related U.S. Application Data

(63) Continuation of application No. 12/447,419, filed as application No. PCT/GB2007/050658 on Oct. 29, 2007, now Pat. No. 8,328,766.

(30) Foreign Application Priority Data

Oct. 27, 2006  (GB) .................................. 0621310.2
Jan. 15, 2007  (GB) .................................. 0700728.9
Mar. 15, 2007  (GB) .................................. 0704952.1

(51) Int. Cl.
*A61M 5/32* (2006.01)
*A61M 5/34* (2006.01)

(52) U.S. Cl.
CPC ........... *A61M 5/3202* (2013.01); *A61M 5/326* (2013.01); *A61M 5/347* (2013.01); *A61M 2005/3247* (2013.01); *A61M 2005/3267* (2013.01)

(58) Field of Classification Search
CPC .................. A61M 5/32; A61M 5/3202; A61M 5/326; A61M 5/347; A61M 2005/3247; A61M 2005/3267

(Continued)

(56) References Cited

U.S. PATENT DOCUMENTS 5,246,428 A   9/1993  Falknor
5,320,609 A   6/1994  Haber et al.
(Continued)

FOREIGN PATENT DOCUMENTS

EP    1535640      6/2005
WO    9531234     11/1995
WO    2006072807   7/2006

OTHER PUBLICATIONS

International Search Report for PCT/GB2007/050658 dated May 29, 2008.

*Primary Examiner* — Theodore Stigell
*Assistant Examiner* — Tiffany Legette
(74) *Attorney, Agent, or Firm* — Grossman Tucker Perreault & Pfleger, PLLC

(57) ABSTRACT

A safety device for shielding the sharp tip of a medical needle has a needle mount which either directly supports a medical needle, or indirectly supports the needle for instance where the needle is provided as a part of a syringe. A sleeve is carried directly or indirectly on the needle mount and is slidably movable to a needle shielding position where the sleeve surrounds the needle sharp tip. A spring including forwardly projecting spring blades when sufficiently loaded acts on an internal conical surface of the sleeve to drive the sleeve to its shielding position and a locking mechanism then locks the sleeve in that position. A camming mechanism serves to load the spring blades in the course of the use of the safety device such that thereafter the interaction of the blades with the conical surface urges the sleeve to its shielding position, the camming mechanism being activated by movement of the sleeve to expose the needle for use.

14 Claims, 21 Drawing Sheets

(58) Field of Classification Search
USPC .................................. 604/192, 193, 197, 198
See application file for complete search history.

(56) References Cited

U.S. PATENT DOCUMENTS

| | | |
|---|---|---|
| 5,634,906 A | 6/1997 | Haber et al. |
| 6,547,764 B2 | 4/2003 | Larsen et al. |
| 6,569,124 B1 | 5/2003 | Perouse |
| 7,001,364 B1 | 2/2006 | Farhi |
| 7,211,069 B2 | 5/2007 | Lehmann |
| 2003/0149404 A1 | 8/2003 | Lehmann |
| 2004/0193110 A1 | 9/2004 | Giambattista et al. |
| 2005/0277893 A1* | 12/2005 | Liversidge .................... 604/198 |
| 2006/0167411 A1 | 7/2006 | Weston et al. |
| 2007/0073224 A1 | 3/2007 | Dries |
| 2007/0129686 A1* | 6/2007 | Daily et al. ................... 604/192 |
| 2008/0103453 A1 | 5/2008 | Liversidge |
| 2009/0326477 A1 | 12/2009 | Liversidge |

* cited by examiner

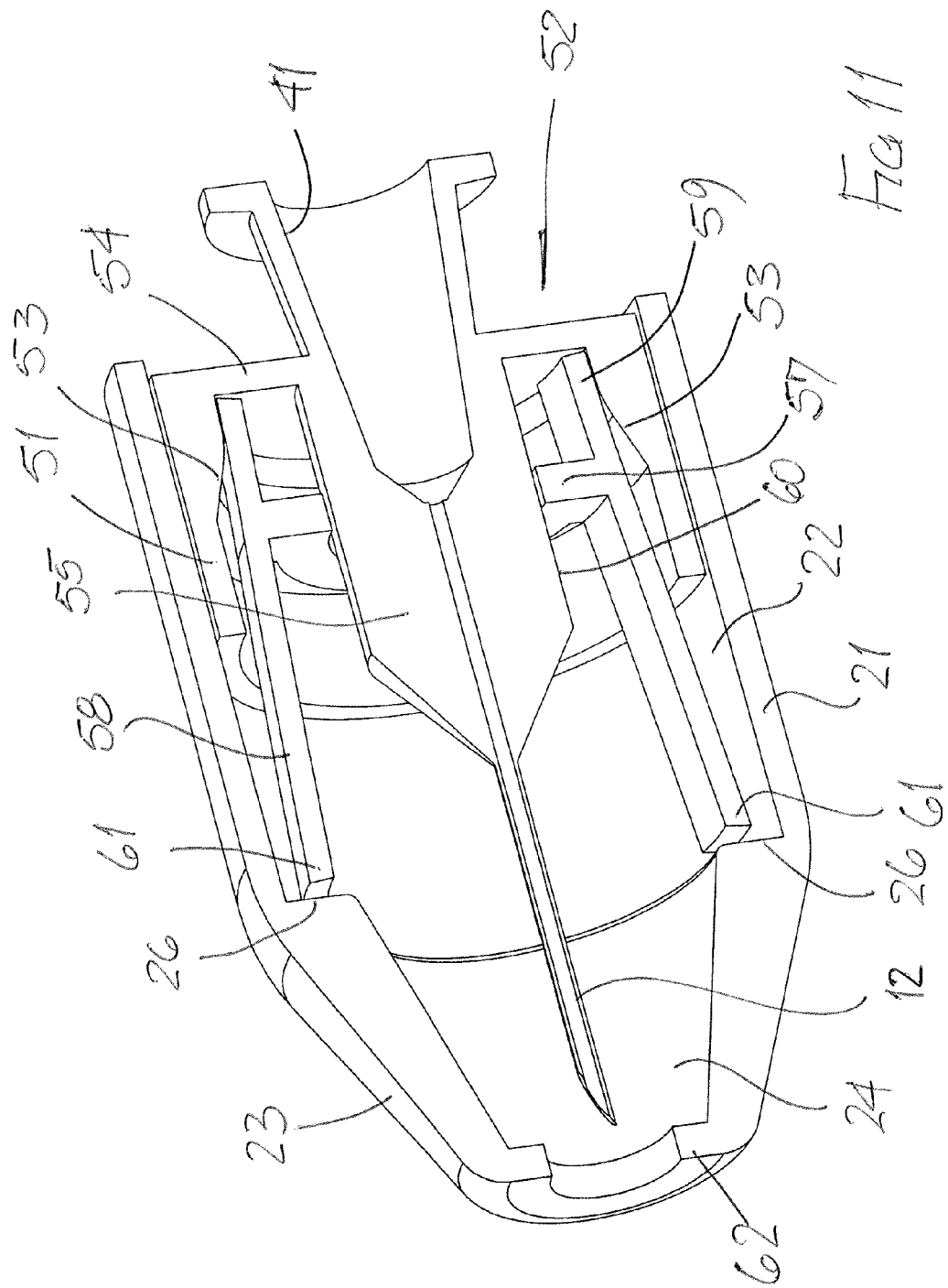

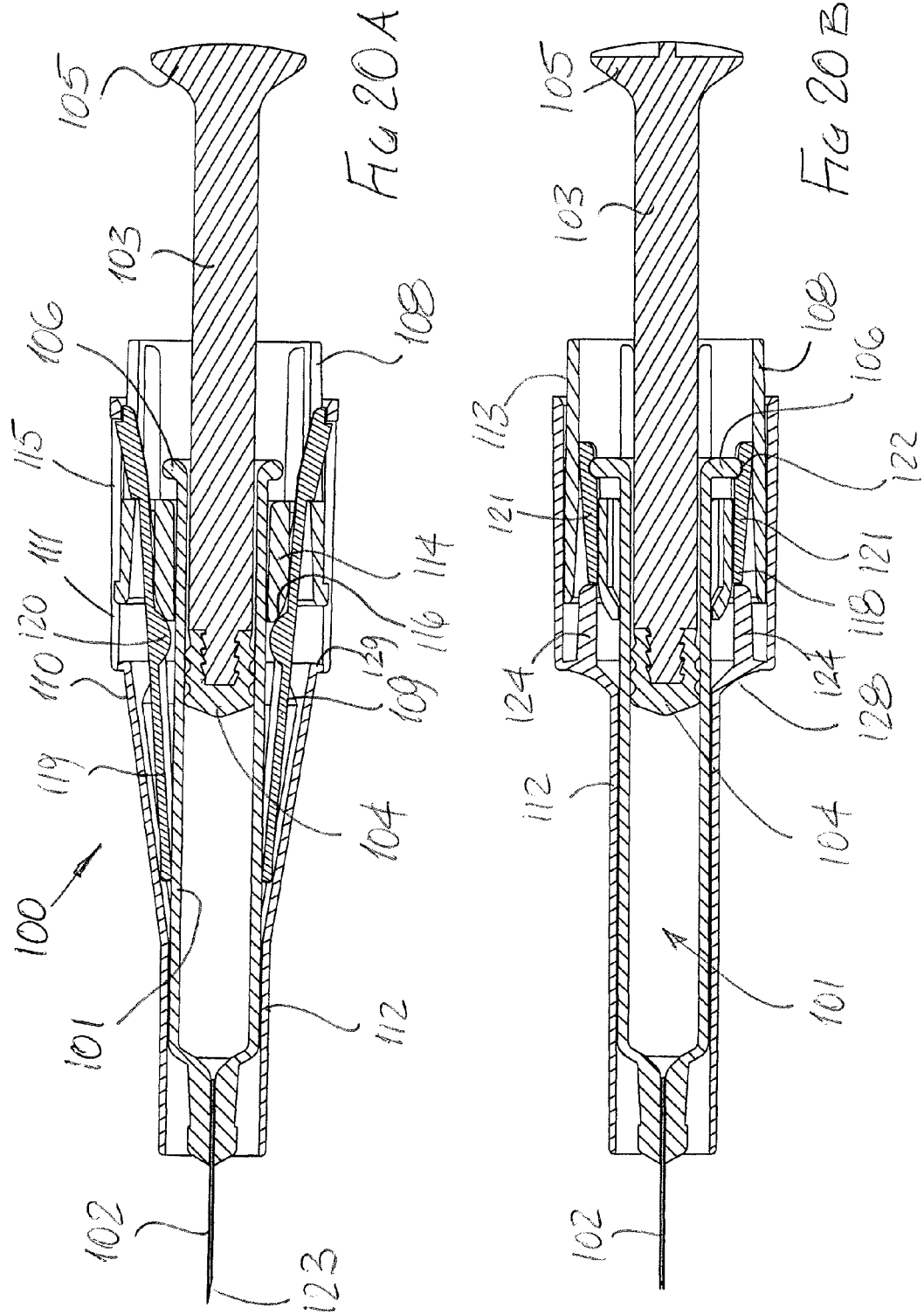

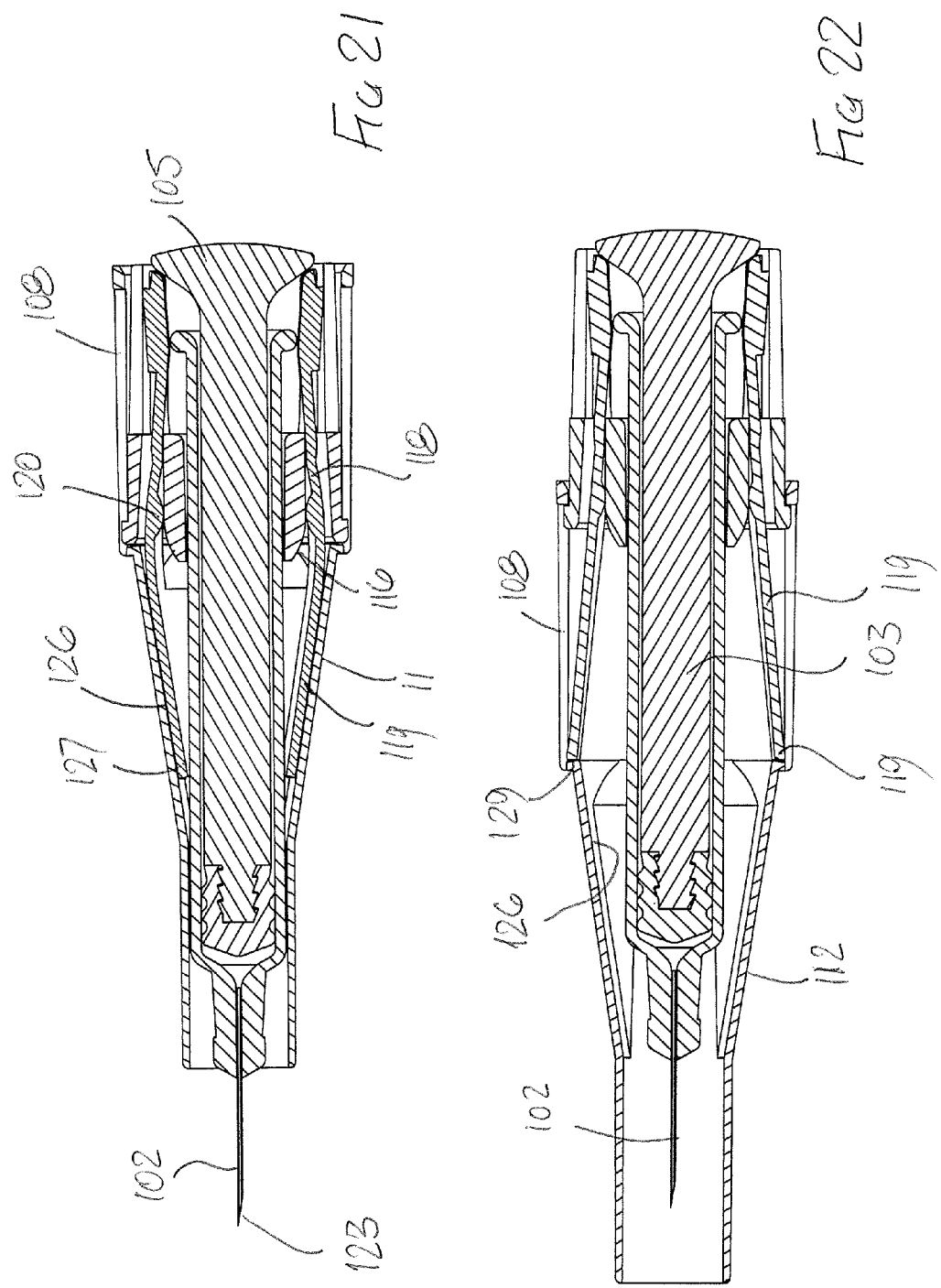

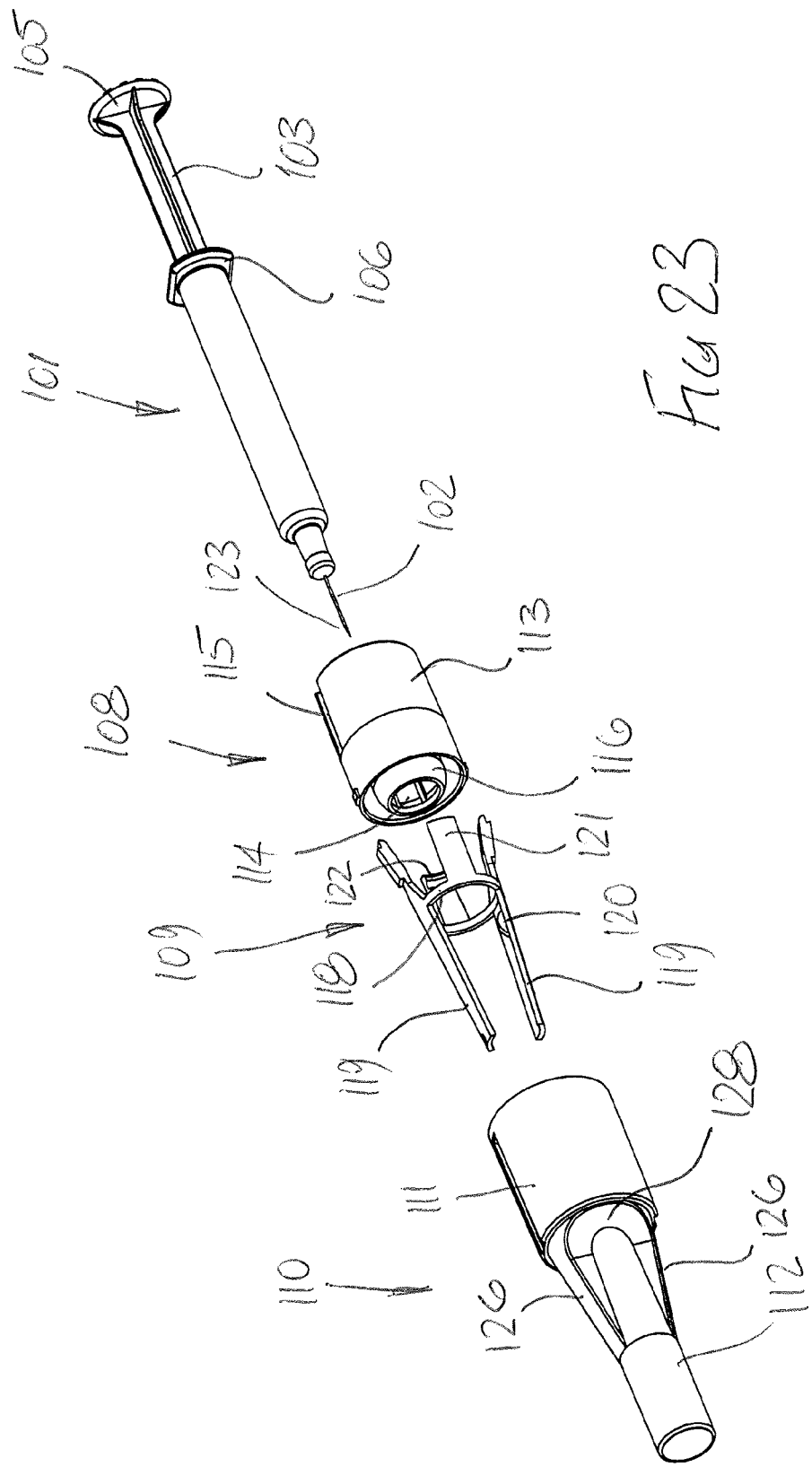

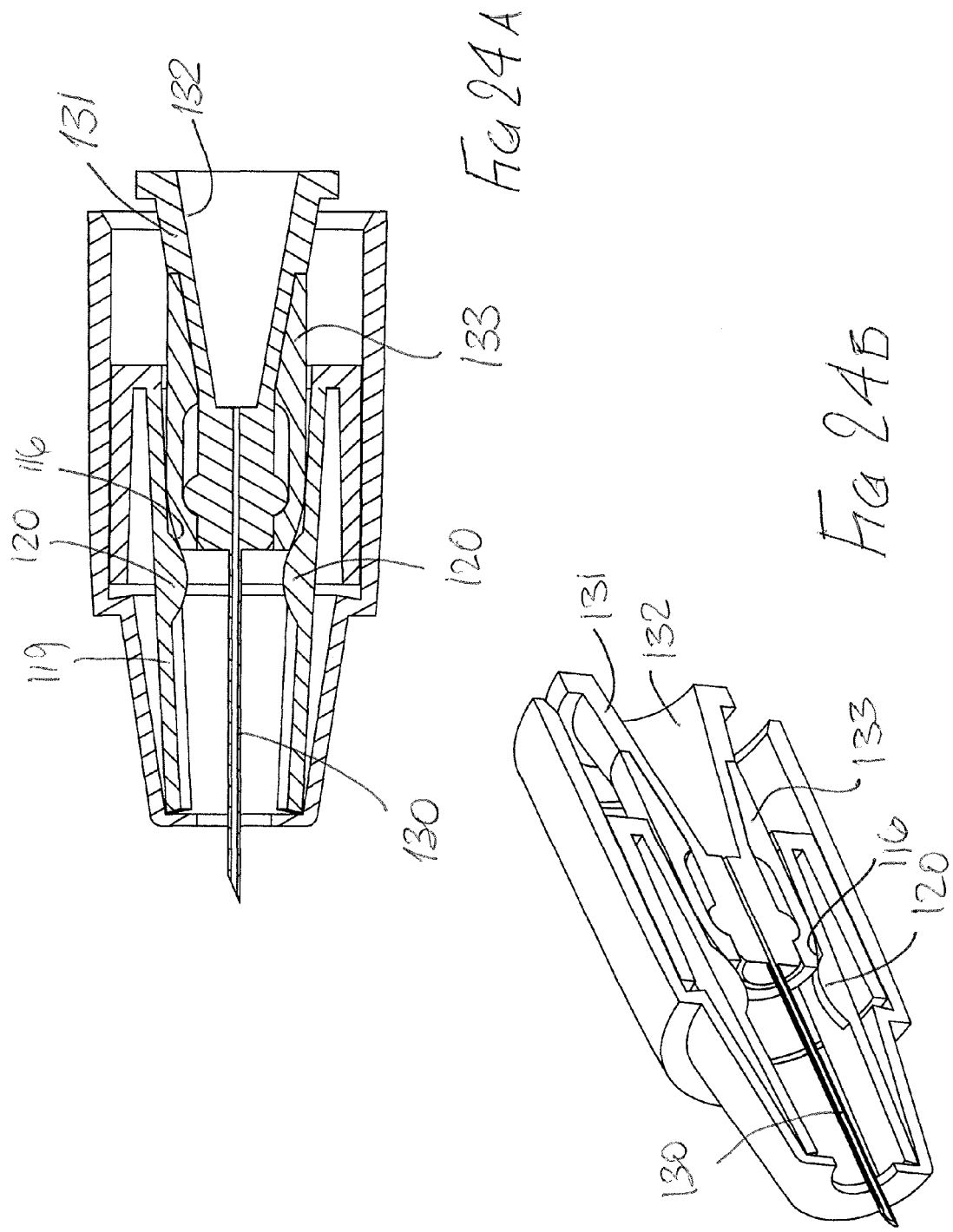

MEDICAL NEEDLE SAFETY DEVICES

CROSS-REFERENCES TO RELATED APPLICATIONS

The present application is a continuation of Application No. 12/447419, filed Apr. 27, 2009, which application was published on Dec. 31, 2009, as U.S.2009/0326477, and which application is the U.S. national stage application of International Application No. PCT/GB2007/050658, filed Oct. 29, 2007, which application was published on May 2, 2008, as WO2008/050158. The international application claims priority to British Application Nos. GB0621310.2, filed Oct. 27, 2006, GB0700728.9, filed Jan. 15, 2007, and GB0704952.1, filed Mar. 15, 2007, the contents of which are incorporated herein by reference in their entireties.

BACKGROUND OF THE INVENTION (1) Field of the Invention

This invention relates to a safety device for a medical needle, to confer passive protection for a needle with which the device is associated. The invention also relates to a safety needle assembly The safety device of this invention has been designed for use with a medical needle having a sharp tip, intended for penetration of a human or animal body, or for other medical uses such as the penetration of a pierceable membrane or of an intravenous medication system. For convenience reference will be made herein solely to the penetration of a body, even though specific embodiments of this invention may be intended for other medical uses.

Throughout this specification, reference is made to the relative terms "forward" and "rearward"; "forward" and "forwardly" refer to the end of the device which is presented to a body when a medical procedure is to be performed (that is, the tip end of the needle) and the direction towards that end; and the terms "rearward" and "rearwardly" refer to the other end of the device (that is, the end of the device nearer a syringe with which the device may be used) and the direction towards that other end.

(2) Description of the Related Art

Fluids of various kinds may be administered to a human or animal body by means of a hollow needle in conjunction with a source of the required fluid. For example, such a needle may be used in conjunction with a syringe holding a liquid drug which may be contained directly in the syringe barrel or in a cartridge located within the syringe, the needle being used to penetrate the body at the site at which the drug is to be received. Equally, body fluids may be withdrawn by using a hollow needle which is used to penetrate the body until the tip is located at the site from which fluid is to be withdrawn.

A recognized hazard for clinicians and other persons using medical needles for the above described purposes, as well as people who may be exposed to used needles in the course of the disposal of those needles, is the risk of a so-called needle-stick injury—that is to say the accidental penetration of a person's skin by the needle. Prior to the use of the needle to supply a fluid to or to withdraw fluid from a body, this rarely presents much of a problem, though once the needle has been used on a body, there is a very much higher risk of a serious consequence for a person suffering a needle-stick injury. During use of the needle to penetrate the body tissues of a patient, the needle is likely to become contaminated with various organisms; should a person subsequently suffer a needle-stick injury, infection could occur.

There have been numerous proposals for protecting the sharp tip of a used needle, in order to reduce the risk of a needle-stick injury following use of the needle. Some proposals have actually increased the likelihood of such an injury by virtue of the action which must be performed to protect the tip, even if the risk thereafter is lessened. Despite all of the proposals which have previously been made, very few have achieved commercial success, nor has there been wide acceptance by the medical industry. Many proposals are somewhat complex and involve a significantly greater manufacturing cost, and so are unacceptable on economic grounds. Others are much more difficult to use as compared to an unprotected needle, and so are rejected by clinicians. Yet further proposals do not allow compliance with best practice protocols.

A device which protects a needle tip after use without an operator having to perform any extra step on withdrawing the needle from a body is usually referred to as a passive protection device. This may be contrasted with an active protection device, where an operator is required to perform an extra step in order to protect a needle, following the withdrawal of the needle from a body. The requirement to perform an extra step leaves the needle unprotected for a longer period than with a passive protection device and further the performance of that extra step exposes the operator to a potentially hazardous situation, when needle-stick accidents can occur There is a significant demand for a passive protection device for use with a needle, and which allows a clinician or perhaps others to use the needle in much the same way as is done with an unprotected needle, but which can be manufactured economically and which provides a high degree of protection against needle-stick injury. In the case of health professionals, this demand is driven by health and safety legislation but in the case of others performing self-injections using a so-called pen injector, the used needles must be disposed of safely with minimum risk to others, even in the event that a sharps container is not immediately available. Further, particularly for self-injections, it is highly preferred that the device operates fully automatically without intervention by the user, so as wholly to prevent access to the needle tip after use other than by a determined attempt to override the protection. In this way, protection may be afforded not just to the clinician or other user of the needle, but also to people who could come into a risky situation with used needles, such as waste disposal operators, cleaners, and so on.

It is often advantageous for a safe needle device having a sleeve to shroud a needle to have an intermediate setting where the needle tip is exposed to a small extent, before use. This is to allow purging of air from the syringe and needle, and also to allow the operator to observe the precise point of penetration of a body. When full protection is to be achieved after performing an injection, the sleeve is moved to a position where the needle is wholly covered, and so to a position further forwardly with respect to the needle than the intermediate setting. If a spring is arranged to provide a force on the sleeve to move it to the final fully-protecting position, that spring will be pre-loaded, when the sleeve is in the intermediate setting.

The pre-loading of a spring is not normally an issue if the spring is of metal. However, to reduce manufacturing costs, it is possible to provide a plastics material spring and in that case, the safe needle device must be stored in such a setting that the spring is not pre-loaded, having regard to the memory effect associated with plastics, especially when stored for long periods. One solution to this problem is by moving the sleeve to the intermediate setting immediately before the safe needle device is to be used to perform an injection. An alternative would be to ensure the spring is not pre-loaded even at the intermediate setting, but arranging the device so that the spring is subsequently loaded during the performance of an injection to provide a sufficient force on the sleeve which will move the sleeve to its protecting position.

The present invention aims at providing a safety needle device for a syringe or other injector which addresses these issues and which is both relatively simple and economic to manufacture, especially on a fully automated production line, and which does not significantly affect a conventional injection procedure when mounted on an injector, including the steps of purging the syringe and needle of air, and observing the needle tip as the needle is inserted in the required injection site.

BRIEF SUMMARY OF THE INVENTION

In its broadest aspect, this invention provides a safety device for shielding the sharp tip of a medical needle, which device comprises the following components:
- a needle support for directly or indirectly mounting a needle;
- a sleeve for protecting the sharp tip of a needle mounted on the needle support, said sleeve being slidably mounted directly or indirectly on the needle support and having a needle shielding position where the sleeve surrounds the sharp tip of a mounted needle;
- a spring separate from the sleeve and arranged to act on the sleeve such that when sufficiently loaded the spring is able to move the sleeve to a needle shielding position; and
- a control arrangement having a clamming surface configured to interact with the spring to increase the loading thereof;
- wherein said components have respective initial positions when the device is ready for use but the spring has insufficient loading to move the sleeve to said needle shielding position, and in the course of use of the device relative movement between the control arrangement and spring from their respective initial positions is arranged to cause the camming surface to interact with the spring to increase the loading thereof and energize the spring sufficiently to exert a spring force on the sleeve capable of moving the sleeve to said needle shielding position.

In another aspect, this invention further provides a safety device for shielding the sharp tip of a medical needle, which device comprises the following components:
- a syringe mounting a needle and having a plunger to expel a liquid drug out of the syringe through the needle;
- a sleeve for protecting the sharp tip of the needle, said sleeve being slidably mounted on the syringe and having a shielding position where the sleeve surrounds the sharp tip of the needle;
- a spring separate from the sleeve and arranged to act an the sleeve such that when sufficiently loaded the spring is able to move the sleeve to the needle shielding position; and
- a control member including a camming surface arranged to interact with the spring to increase the loading thereof:
- wherein said components have respective initial positions when the device is ready for use but the spring has insufficient loading to move the sleeve to said needle shielding position, and the syringe and control member are arranged so that in the course of use of the device the plunger comes into engagement with and moves the control member relative to the spring to cause the camming surface to interact with the spring and increase the loading thereof thereby to energize the spring sufficiently to exert a spring force on the sleeve capable of moving the sleeve to said needle shielding position.

BRIEF DESCRIPTION OF THE SEVERAL VIEWS OF THE DRAWINGS

Several specific embodiments of safety device of this invention will be described in detail, reference being made to the accompanying drawings. In the drawings:

FIGS. 9, 10 and 11 correspond to FIGS. 6, 7 and 8 but show the third embodiment in similar positions;

FIGS. 20A and 20B are axial sections taken at 90° to each other, through an eighth embodiment, intended for use with a pre filled syringe, these Figures showing the embodiment when ready for use;

FIG. 21 is an axial section corresponding to FIG. 20A but when an injection has been completed:

FIG. 22 is a further axial section but showing the device following the completion of an injection and with the sleeve locked in a protecting position;

FIG. 23 is an exploded view of the components of the eighth embodiment; and

FIGS. 24A and 24B are respectively axial and isometric sectional views on a ninth embodiment, when ready for use.

Figure 1:
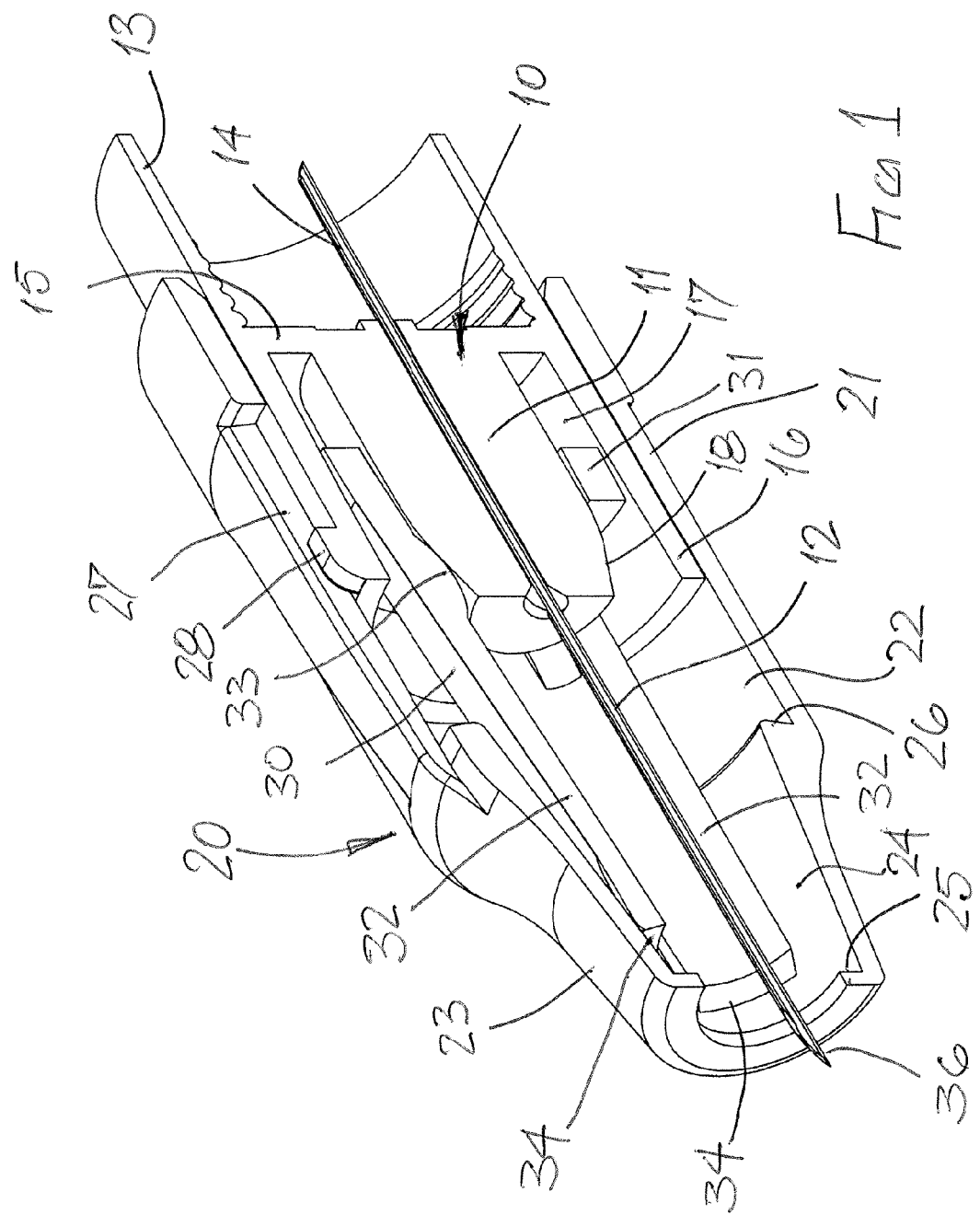
FIG. 1 is an isometric axial sectional view of the first embodiment, with the components in their initial positions, ready to perform an injection.
Figure 2:
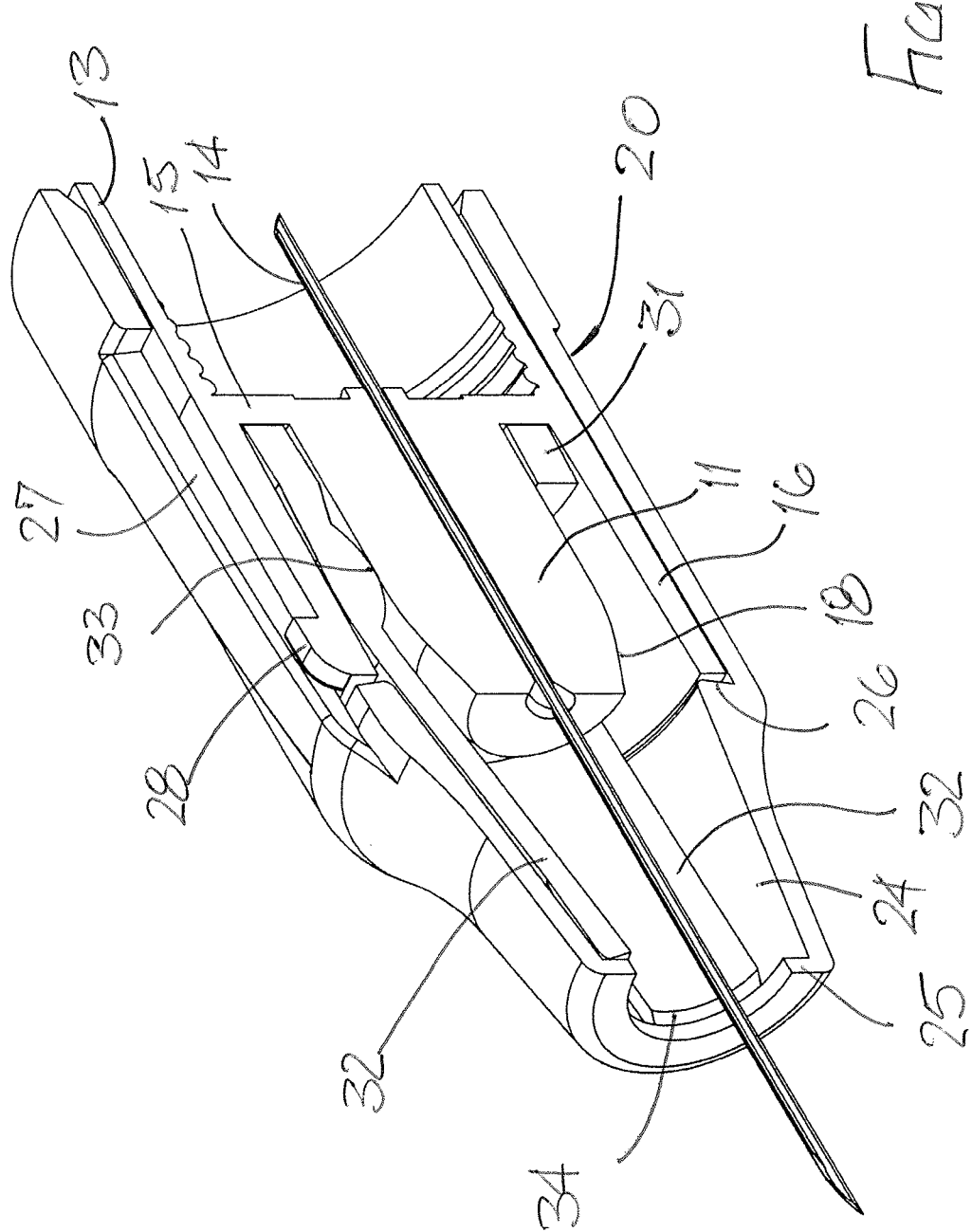
FIG. 2 is similar to FIG. 1, but showing the components in their relative positions when an injection is being performed.
Figure 3:
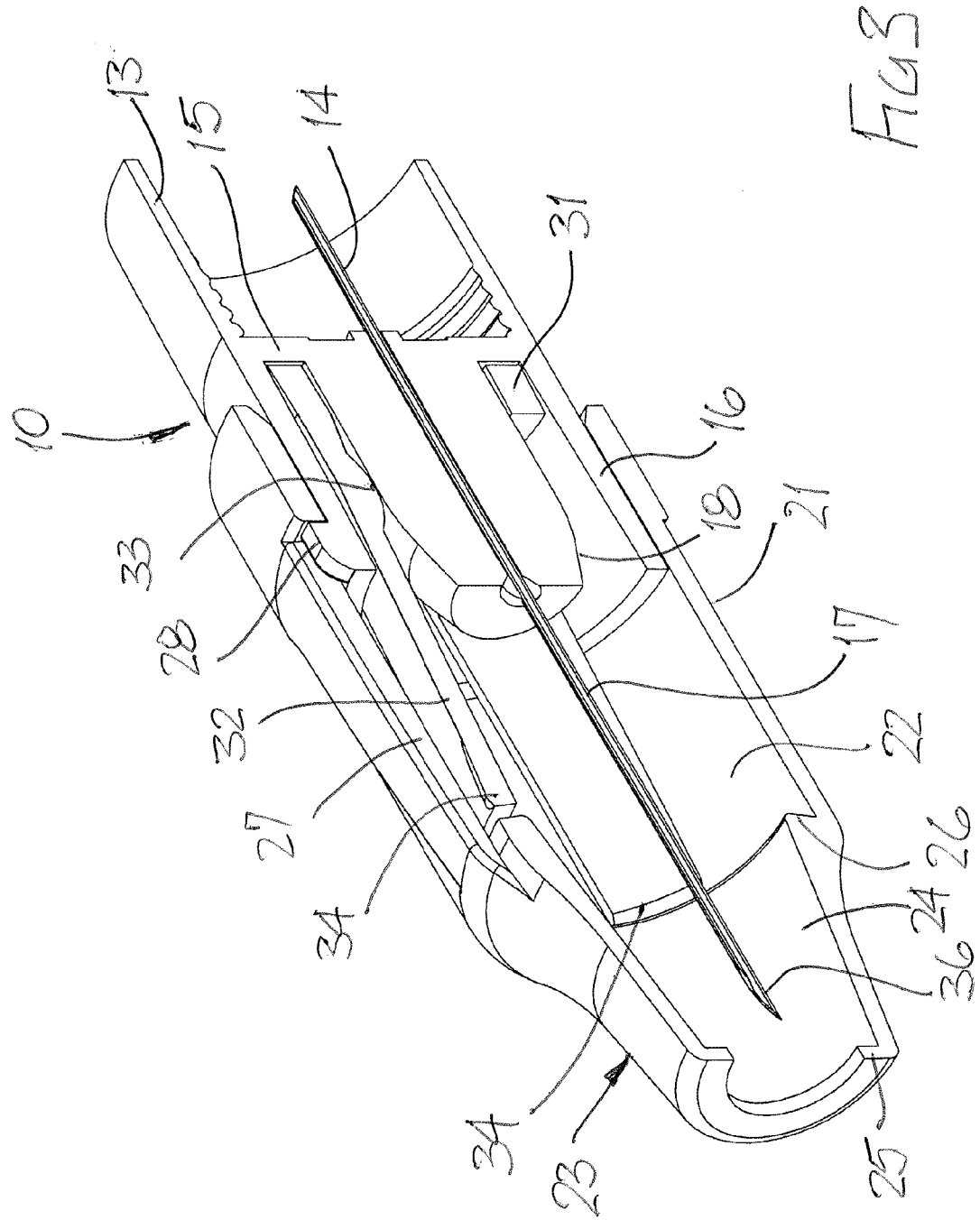
FIG. 3 is similar to FIG. 1, but showing the sleeve locked out following the performance of an injection.

In the following description, the term carrier is used interchangeably with the term "needle support" used hereinbefore; similarly, the term "protecting position" is used interchangeably with the term "shielding position" used hereinbefore.

DETAILED DESCRIPTION OF THE INVENTION

Embodiments of this invention may include a spring which, in an initial setting of the device, exerts no bias on the components between which the spring acts. Then, during the course of performing a procedure with which the device is associated, the control member serves to load or energise the spring by the deformation thereof, so that thereafter the spring exerts a spring force on the sleeve capable of moving the sleeve to its shielding position. In preferred embodiments, the sleeve is locked in that shielding position so as to prevent subsequent movement of the sleeve away therefrom.

Such embodiments lend themselves for use with a spring of a plastics material, since the spring will not be stressed when the device is in its initial position. Preferably, the spring comprises a spring blade formed from a plastics material and which, when loaded, acts on a surface of the sleeve inclined to the axis thereof, thereby to apply a bias to the sleeve along the sleeve axis in the direction of the shielding position.

Most preferably, there is a locking mechanism for the sleeve, one part of the locking mechanism being provided on the sleeve and there being a locking member which may interact with said one part to lock the sleeve when in its shielding position, so as to prevent movement of the sleeve away from that shielding position.

A preferred embodiment of this invention provides a single-use safety device for a medical needle having a sharp tip, which device comprises:
 a needle support for directly or indirectly mounting a needle;
 a sleeve slidably mounted directly or indirectly on the needle support and having an open-ended rearward portion defining an essentially parallel bore and an open ended forward portion of a smaller internal size than the rearward portion and of a reducing cross-sectional area in the forward direction for at least part of the length of the forward portion, the sleeve having a shielding position where the forward portion fully surrounds the tip of a mounted needle, the sleeve further being provided with one part of a locking mechanism formed between the rearward and forward portions of the sleeve;
 a spring arranged within the sleeve so that when loaded the spring urges the sleeve towards its shielding position;
 a locking member positioned within the sleeve and arranged to interact with said locking mechanism for locking the sleeve in its shielding position; and
 a control arrangement which when activated loads the spring thereby causing the sleeve to move towards its shielding position and allowing the locking member to lock the sleeve in said shielding position, said control arrangement being activated by relative movement of the sleeve and needle support.

Embodiments of safety device of this invention particularly lend themselves for use with a syringe pre-filled with a drug and furnished with a needle, so as to be ready for performing an injection. The device may however be used with other needle supports, such as those used with an auto-injector.

The safety device allows the use of a plastics material spring which cannot ordinarily be pre-loaded before storage since the spring will gradually lose its spring force. With this invention, the spring may initially be in an unloaded condition and as such incapable of producing any biasing force until the control arrangement is activated, whereafter the spring becomes loaded to urge the sleeve to move towards its shielding position.

With the safety device of this invention, the initial position of the sleeve with respect to the needle support may be the same as the final shielding position of the sleeve, and so wholly covering the sharp tip of the needle, or may be displaced from the shielding position, whereby the sharp tip of the needle is exposed when the sleeve is in the initial position. If the initial position of the sleeve wholly covers the sharp tip of the needle, then there may be an intermediate position of the sleeve with respect to the needle support, where the sharp tip of the needle is exposed sufficiently to permit purging of the syringe and needle and also observation of the precise entry point of the needle at the injection site. In such a case, it is preferred that the spring force urging the sleeve forwardly with respect to the needle support is not generated by the control arrangement until the sleeve is moved further rearwardly from the intermediate position.

In an embodiment of this invention, the spring also serves as a locking member and has a resilient finger which when loaded serves to urge the sleeve to its shielding position upon activation of the control arrangement to urge the forward end of the finger outwardly to bear against an inwardly tapering internal surface of the sleeve. When the components are in their initial positions, the resilient finger is in a relaxed state and so is not deformed. On the sleeve performing relative movement with respect to the needle support to perform an injection, the spring is loaded by deforming the finger such that the finger thereafter serves to urge the sleeve forwardly relative to the needle support and the force is maintained on the sleeve until locked in its shielding position.

Preferably, the spring also has an initial position relative to the needle support and sleeve where the resilient finger is essentially unstressed and the forward end of the finger is at or adjacent the forward end of the sleeve, and the spring has freedom of movement axially rearwardly with respect to the needle support. In this case, an interacting camming arrangement may be formed on the needle support and on the spring and arranged so that on relative movement between the needle support and the sleeve from said initial position when performing an injection thereby exposing the needle, the finger is resiliently deformed so that the forward end thereof bears on the tapering forward portion of the sleeve. This generates a force on the sleeve urging the sleeve forwardly with respect to the needle support, so that on completion of the injection, the sleeve is driven to the shielding position where the forward end of the finger engages said abutment thereby preventing subsequent rearward movement of the sleeve with respect to the needle support.

The required movement of the needle support relative to the sleeve before the camming arrangement serves to deform the finger may be pre-set in order to allow the provision of an intermediate setting for the sleeve, as discussed above. In the alternative, the camming arrangement may start to operate on the finger immediately the sleeve starts to move from its initial position to cause the needle to project from the sleeve.

Preferably, the sleeve is generally tubular with a substantially cylindrical rearward portion, a substantially conical forward portion and an abutment being formed at the junction between those two portions. The needle support may then be mounted within the rearward portion of the sleeve for sliding movement with respect thereto along the axis of the sleeve. In a preferred embodiment, the needle support has an inner hub for supporting the needle and a tubular part surrounding at least part of the hub to define an annular space therebetween, the outer surface of the tubular part being slidably received in the rearward portion of the sleeve. In this case, the rearward end of the spring may be accommodated within that annular space.

In one embodiment, the spring has an annular base from which a plurality of resilient fingers, and preferably two or three fingers, project forwardly from said base located in the annular space. In this case, the inwardly directed face of each finger may include a camming surface such as a rounded projection, adapted to engage a profiled part of the hub. Rearward movement of the spring relative to the hub will cause the rounded projections to ride up the profiled part thereby resiliently deforming the fingers, so that the forward ends thereof move outwardly to bear on the internally tapered forward portion of the sleeve. In this way, the resilient force provided by the deformed fingers will urge the sleeve forwardly with respect to the needle support. Preferably, the profiled part of the hub comprises a conical surface, whereby the relative angular orientation between the locking member, the needle support and the sleeve is not material.

In an alternative embodiment, the spring has an annular support carrying a plurality of fingers, each projecting forwardly and rearwardly of the annular support. In this embodiment, the annular space defines a camming surface for engagement by a rearwardly projecting part of each finger, whereby rearward movement of the spring relative to the needle support causes resilient deformation of the fingers with the annular support acting as a fulcrum for those fingers. In this way the forward ends of the fingers are caused to bear on the inwardly tapered forward portion of the sleeve, thereby urging the sleeve forwardly with respect to the needle support. Preferably, the camming surface is formed internally within the tubular part of the needle support, surrounding the hub. The hub itself may have a cylindrical portion on which the annular support of the spring is slidably received.

With the safety device of this invention, the needle support may have a tapered socket such as a Luer slip or Luer lock socket, for connection to a correspondingly tapered spigot provided at the forward end of an injector. In the alternative, for a safety device for use for example with a pen injector, the needle support may have an internally threaded socket for connection to a correspondingly threaded spigot provided at the forward end of the injector. For such a device, the needle may be double-ended and project rearwardly into the socket, for communication with the septum of a vial of medicament contained within an injector to which the device is connected.

For a safety device having a screw-threaded socket, it is advantageous for there to be means to prevent relative rotation between the sleeve and the needle support. For example, one or more slots may be formed in the sleeve and which extend parallel to the axis thereof, and the needle support has a respective lug for each slot thereby to restrain relative rotation between the needle support and the sleeve.

Other preferred embodiments of safety device of this invention utilise a sleeve wherein the inclined forward surface tapers towards the forward end of the sleeve and so may be of generally conical form, at least for part of the internal circumference of the forward portion of the sleeve. In the alternative, the inclined surface may be generally helically formed, about the axis of the sleeve. A further possibility is for the inclined surface to be substantially planar and to be oblique to the axis of the sleeve. With these last two possibilities, the resilient finger may be deformed in the circumferential direction by the action of the control arrangement, whereby the force of the forward end of the finger on the inclined forward surface is increased, so providing the force which moves the sleeve to its shielding position. The finger is resiliently deformed towards the inclined forward surface thereby urging contact of the forward end of the finger against the forward surface.

As discussed above, the part of the forward portion of the sleeve of a reducing cross-sectional area may comprise a forwardly tapered internal surface within the forward portion, and forwardly of that tapered internal surface, the sleeve may have a substantially parallel portion within which a needle support (such as a syringe) may be slidably mounted.

The control arrangement may comprise co-operating camming surfaces on the needle support and on the leaf spring, arranged to move the forward end of the leaf spring towards the tapered internal surface. The needle support when moved sufficiently forwardly with respect to the leaf spring during use of the device thereby loads the leaf spring causing said spring to remain in its loaded condition throughout subsequent use of the device.

In an embodiment where the device is arranged for use with a syringe, it is preferred for the spring to interconnect to the syringe to limit relative movement therebetween. Then, during a last stage of drug delivery from a syringe, the plunger of the syringe may move forwardly the camming surface of the control arrangement thereby loading the spring.

It is known to provide a safety device for a medical needle with an indicator which serves to show whether the device is ready for use with the protecting sleeve (or shield) in a forward position surrounding the needle, or whether the device has been used and the sleeve has been locked in its forward shielding position. It is possible to provide the safety device of this invention with such an indicator but the indicator may be arranged so as to show when the sleeve is fully withdrawn and with the needle fully exposed. Particularly in the case of a pen needle injector when provided with a safety device as just described, the indicator may then serve to show when the needle has penetrated a patient to the required full extent, with the forward end of the sleeve abutting the patient's skin.

Another embodiment of this invention provides a safety device with an indicator which serves to show when the needle has penetrated a patient to the required extent, as well as showing when the device is ready for use and when it has been used with the protecting sleeve locked in a shielding position.

The specific embodiments shown in the drawings will now be described.

Referring initially to FIGS. 1 to 5, there is shown a safety pen needle device intended for use with a so-called pen injector, primarily for use in the self-administration of medicaments, such as is widely employed with insulin. The device comprises a carrier 10 having a hub 11 supporting a needle 12 projecting both forwardly from the hub and rearwardly into an internally threaded tubular extension 13 of the carrier, by means of which the carrier may be secured to the externally threaded spigot at the forward end of a pen injector (not shown). On mounting the carrier 10 in this way on a pen injector, the rearward part 14 of the needle 12 penetrates the bung of a vial (not shown) of medicament within the injector. The details of such a pen injector are well known in the art and will not be described further here.

The hub 11 includes a flange 15 at its rearward end, by means of which the hub is connected to the tubular extension 13. Projecting forwardly from the flange 15 is a tubular part 16 the outer surface of which is continuous with that of the tubular extension 13, an annular space 17 being defined between that part 16 and the hub 11. The forward end portion of the hub is formed with a conical outer surface 18 serving as a control member, for a purpose to be described below.

Slidably carried on the outer surface of the extension 13 and tubular part 16 is a sleeve 20 having a rearward portion 21 defining a parallel bore 22 and a forward portion 23 which defines an conical internal surface 24 having at its forward end an in-turned lip 25. An internal annular rearwardly facing abutment 26 is formed between the rearward and forward portions 21 and 23 of the sleeve 20. Three axially extending slots 27 are formed in the sleeve 20, in each of which is received a respective lug 28 formed at the forward end of the tubular part 16 of the carrier 10 whereby the carrier 10 and sleeve 20 are held against relative angular rotation. In this way, turning of the sleeve allows the carrier 10 to be threaded on to and off the threaded spigot of a pen injector.

Disposed within the sleeve 20 is a spring and locking member 30 having an annular base 31 dimensioned to be a free sliding fit within the space 17. Three resiliently deformable fingers 32 project forwardly from the base 31 and each of those fingers has a ramming surface 33 provided at such a position that the surface overlies the conical outer surface 18 of the hub 11 when the device is in its initial setting as shown in FIG. 1. In this initial setting, the forward ends 34 of the fingers 32 lie closely adjacent the lip 25 at the forward end of the sleeve 20. The spring and locking member 30 is moulded from a plastics material of a suitable quality and grade so as to allow the fingers 32 to be resiliently deformed from their initial position as shown in FIG. 1. When the device is set as shown in that Figure, the spring and locking member 30 is unstressed and so essentially in an as-moulded condition.

Though not shown in the drawings, it would be possible for the device to have a storage position, where the sleeve 20 is further forwardly of the carrier 10 than is shown in FIG. 1, so that the forward end of the sleeve wholly surrounds the tip 36 of the needle 12. Both in such a position and in the initial position of FIG. 1, the spring and locking member is unstressed and so if the fingers 32 are resiliently deformed from that unstressed condition, the fingers then provide a restorative force to their initial condition.

In the initial setting of FIG. 1, the tip of the needle is visible and so, when connected to an injector device, allows sight of the needle tip for purging, and also subsequently for viewing the injection site. On performing an injection, the sleeve 20 is moved rearwardly with respect to the carrier 10. Initially, the forward ends 34 of the fingers 32 come into engagement with the lip 25 and then the spring and locking member 30 is moved rearwardly until the annular base 31 of the spring and locking member comes into engagement with the flange 15 of the carrier 10. This defines the injecting position with the needle 12 projecting to its greatest extent beyond the forward end of the sleeve 20.

Figure 4:
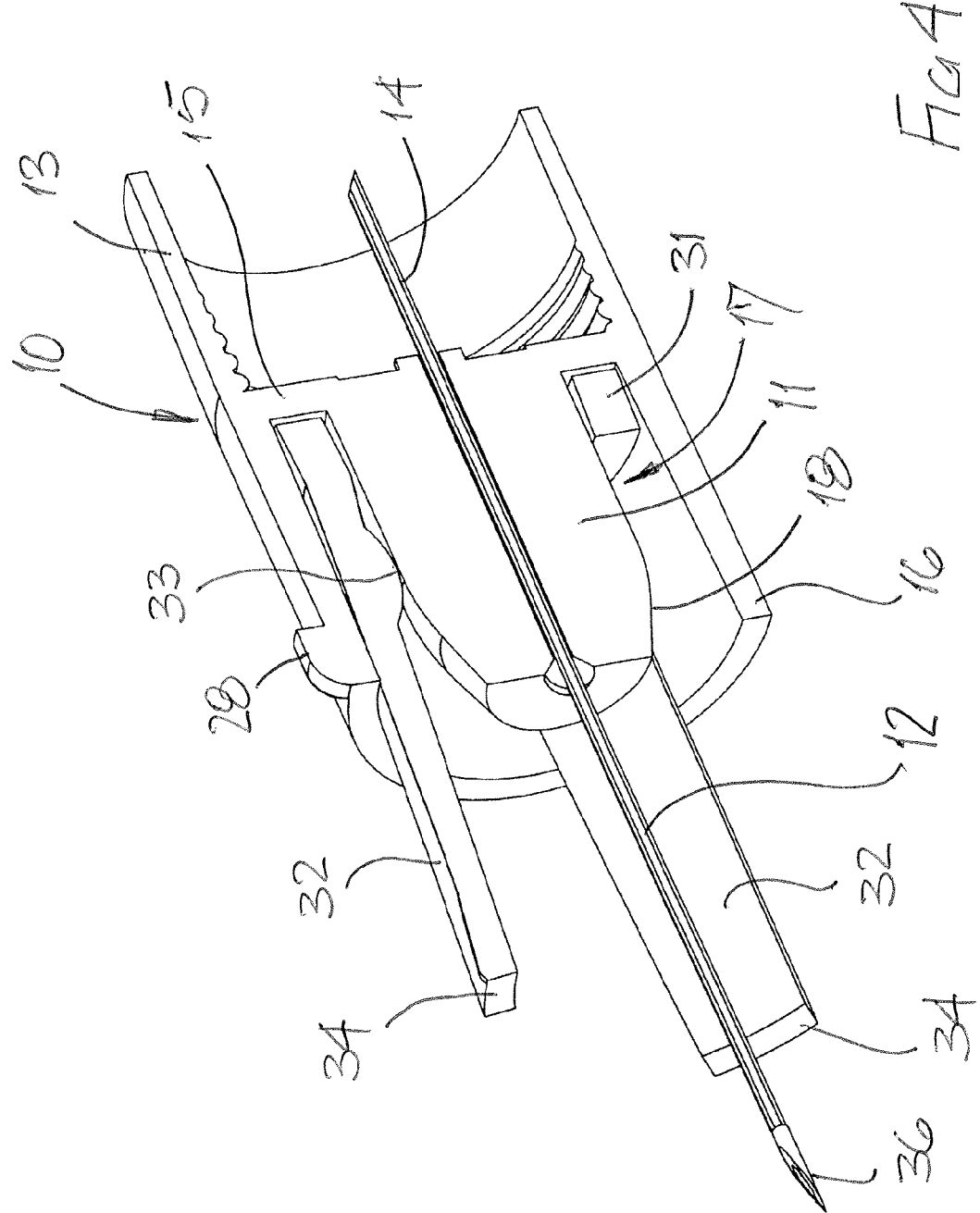
FIG. 4 shows the needle support and spring member, also serving as a locking member, in their relative positions corresponding to FIG. 2, but with the sleeve removed.
Figure 5:
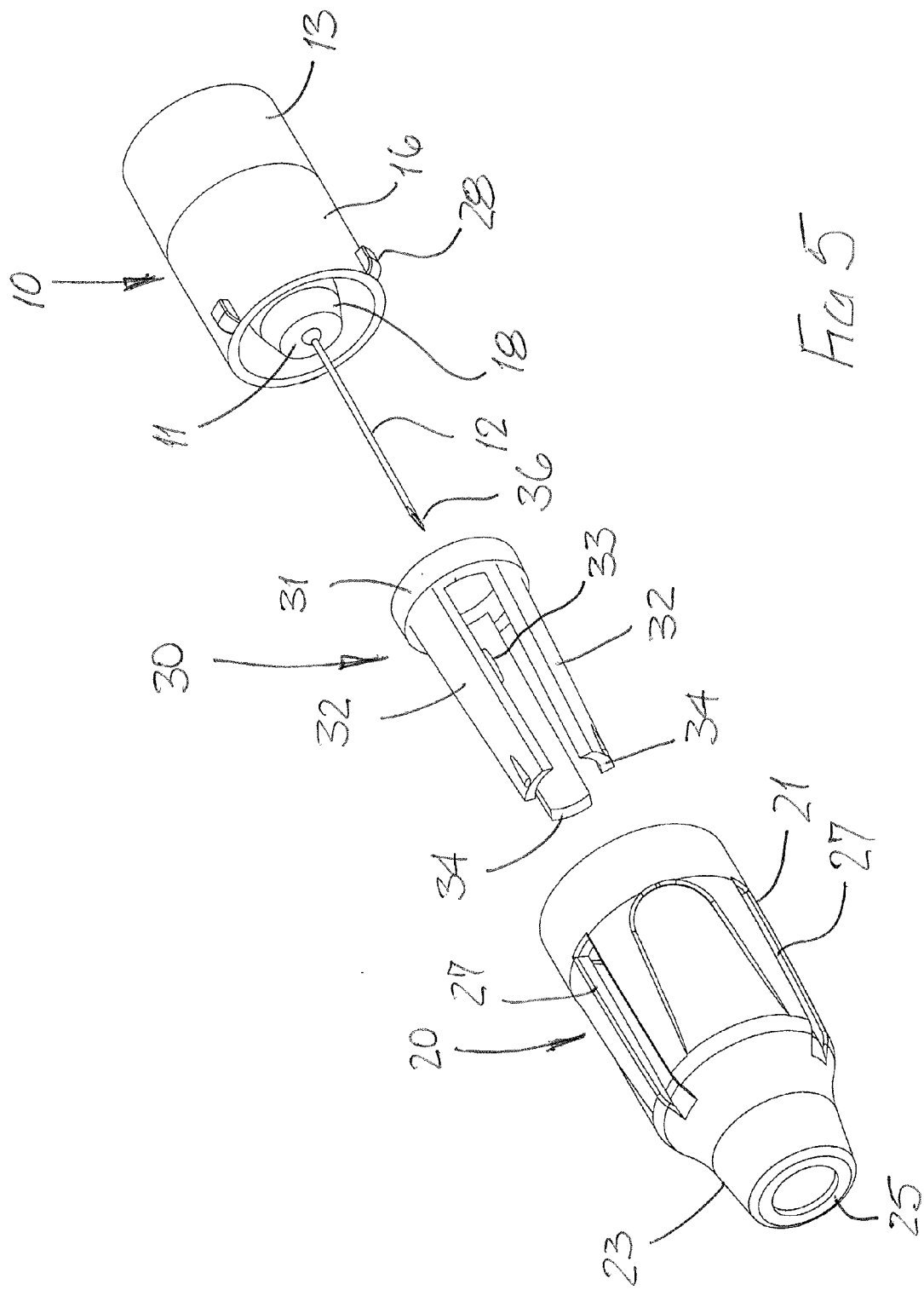
FIG. 5 is an isometric exploded view of the first embodiment.

Once the forward ends 34 of the fingers 32 engage the lip 25, the spring and locking member 30 is moved rearwardly with respect to the carrier 10 so driving the camming surfaces 33 up the conical outer surface 18 of the hub 11 until those camming surfaces 33 ride on the cylindrical part of the hub. The annular base 31 constrains the rearward ends of the fingers and thus this action resiliently deforms the fingers. Were the forward ends of the fingers not constrained by the forward end of the sleeve 20, the forward ends would spring outwardly, as shown in FIG. 4; the forward ends of the fingers are thus in effect deformed resiliently radially inwardly and apply a restorative force to the conical internal surface 24 of the sleeve 20.

On completion of the injection, by moving the device away from a patient, that restorative force urges the sleeve 20 forwardly with respect to the carrier 10 by virtue of the forward ends 34 of the fingers 32 bearing on the conical internal surface 24 of the sleeve 20, that restorative force also maintaining the base 31 in engagement with flange 15 of the hub 11. The sleeve 20 is moved fully forwardly to the extent permitted by the lugs 28 in the slots 27, at which position the forward ends 34 of the fingers engage behind the abutment 26 and thus lock the sleeve against subsequent rearward movement with respect to the carrier 10. By appropriate profiling of the hub and spring and locking member, the forward ends of the fingers may still be resiliently deformed to a small extent when this position is reached, so that the forward ends of the fingers will be maintained in engagement with the bore 22 of the sleeve 20.

Figure 6:
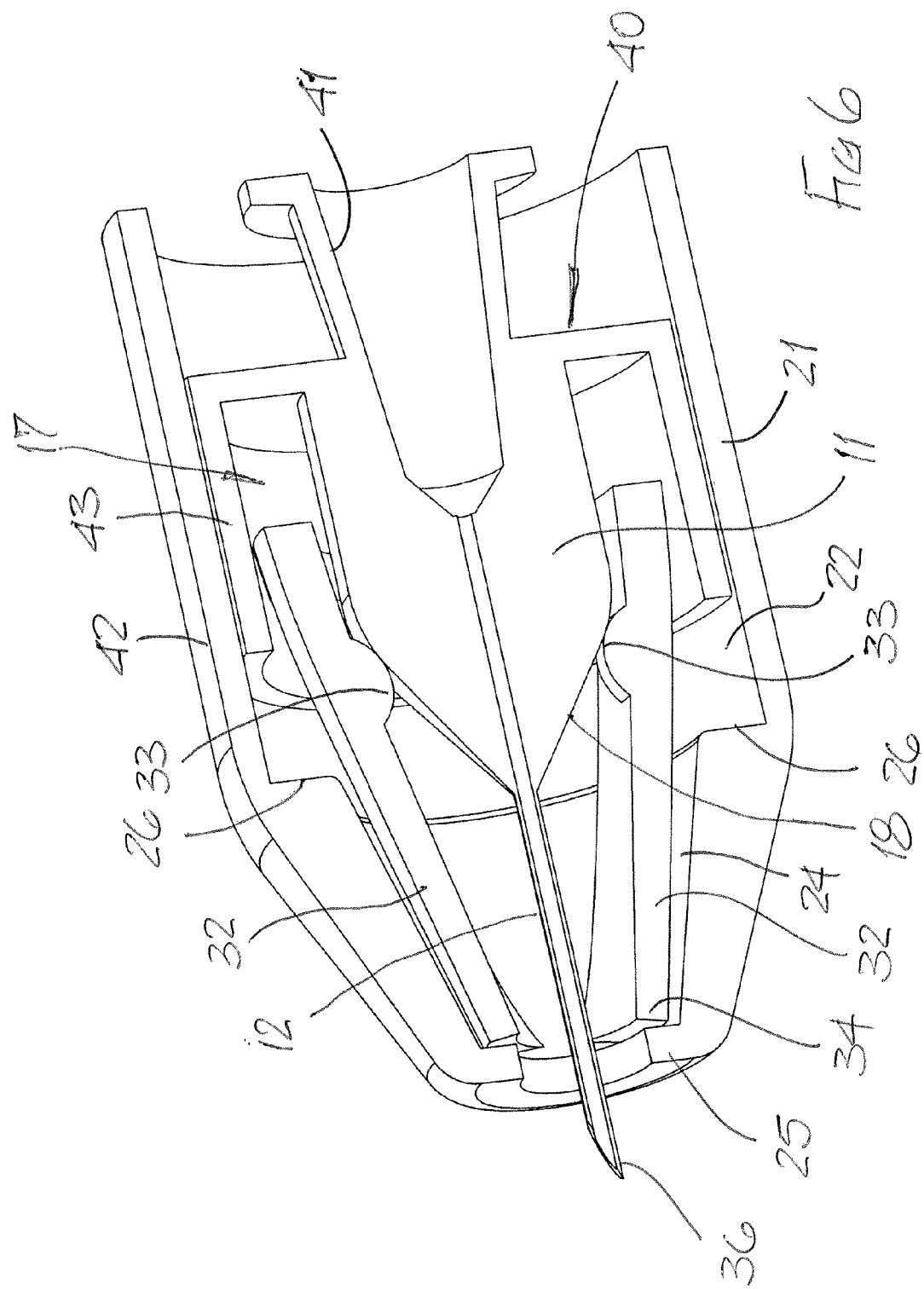
FIGS. 6, 7 and 8 show the second embodiment, respectively in an initial (ready to inject) position injecting position and protecting position where the sleeve is locked against rearward movement.
Figure 7:
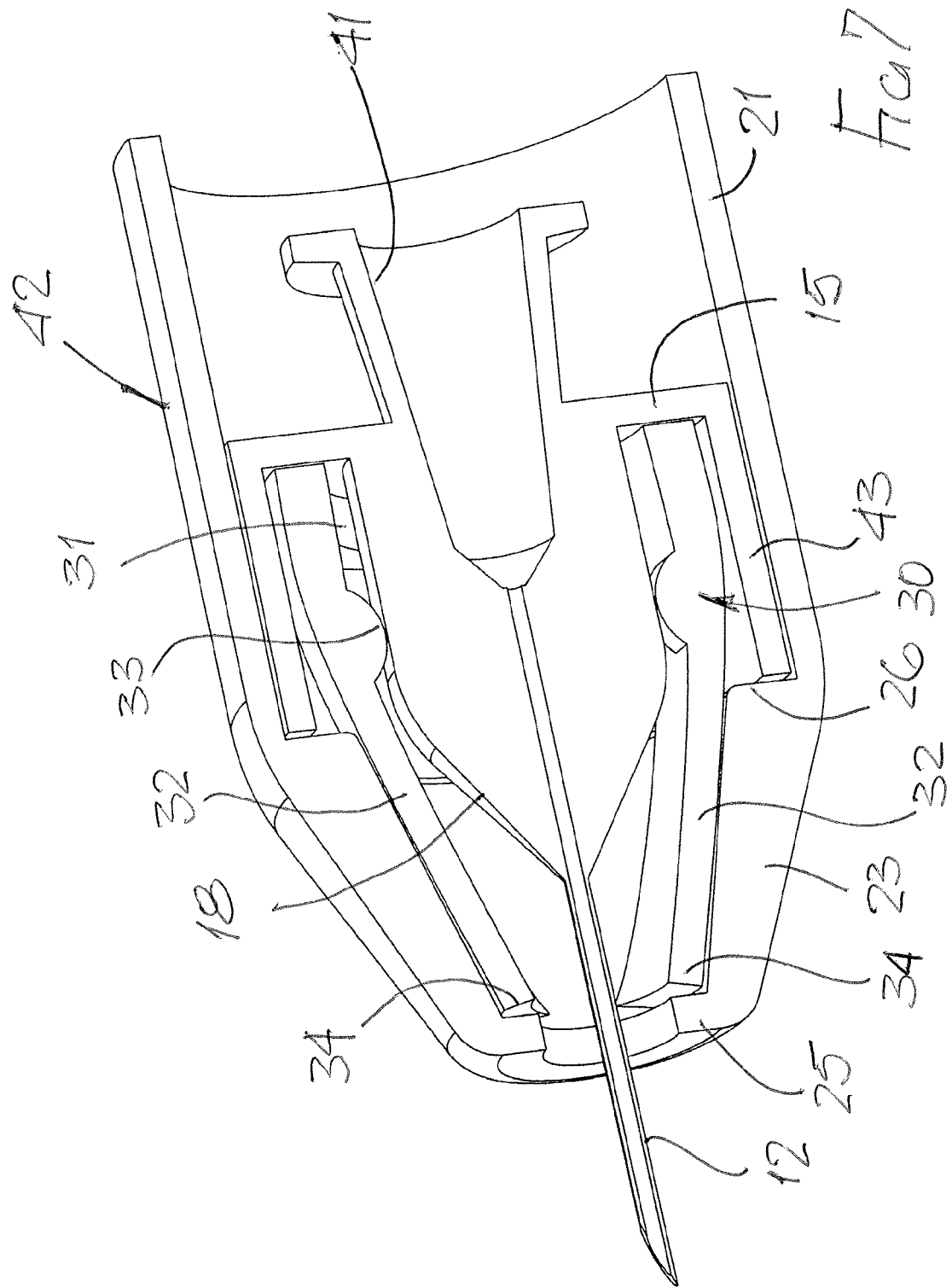
Figure 8:
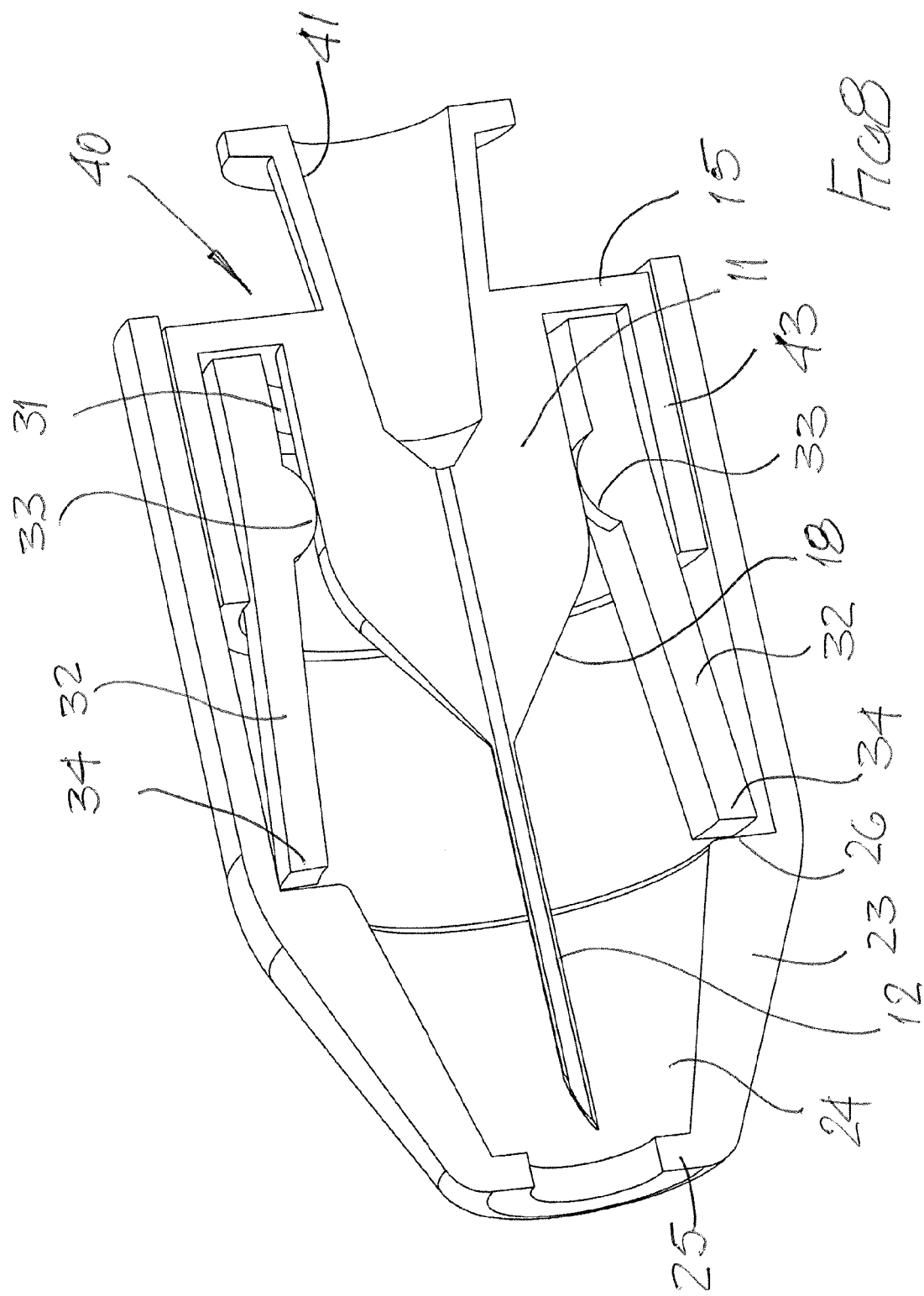

FIGS. 6 to 8 show a second embodiment the constructional details of which are similar to those of FIGS. 1 to 5 and so this second embodiment will not be described in detail, here. Like parts, or similar parts having essentially the same function to those of FIGS. 1 to 5, are given the same reference numbers. As compared to the first embodiment, the second embodiment has a carrier 40 having a Luer slip socket 41 at its rearward end, for connection to a Luer slip spigot formed at the forward end of a syringe (not shown). The carrier 40 does not have a rearward tubular extension, the sleeve 42 being supported solely on tubular part 43 of the carrier 40. Further, the carrier does not have to be restrained against relative rotation with respect to the sleeve 42 and thus no interengaging lugs and slots are provided.

In other respects, this second embodiment is closely similar to that described above with reference to FIGS. 1 to 5 and it will not therefore be described again in detail here.

Figure 9:
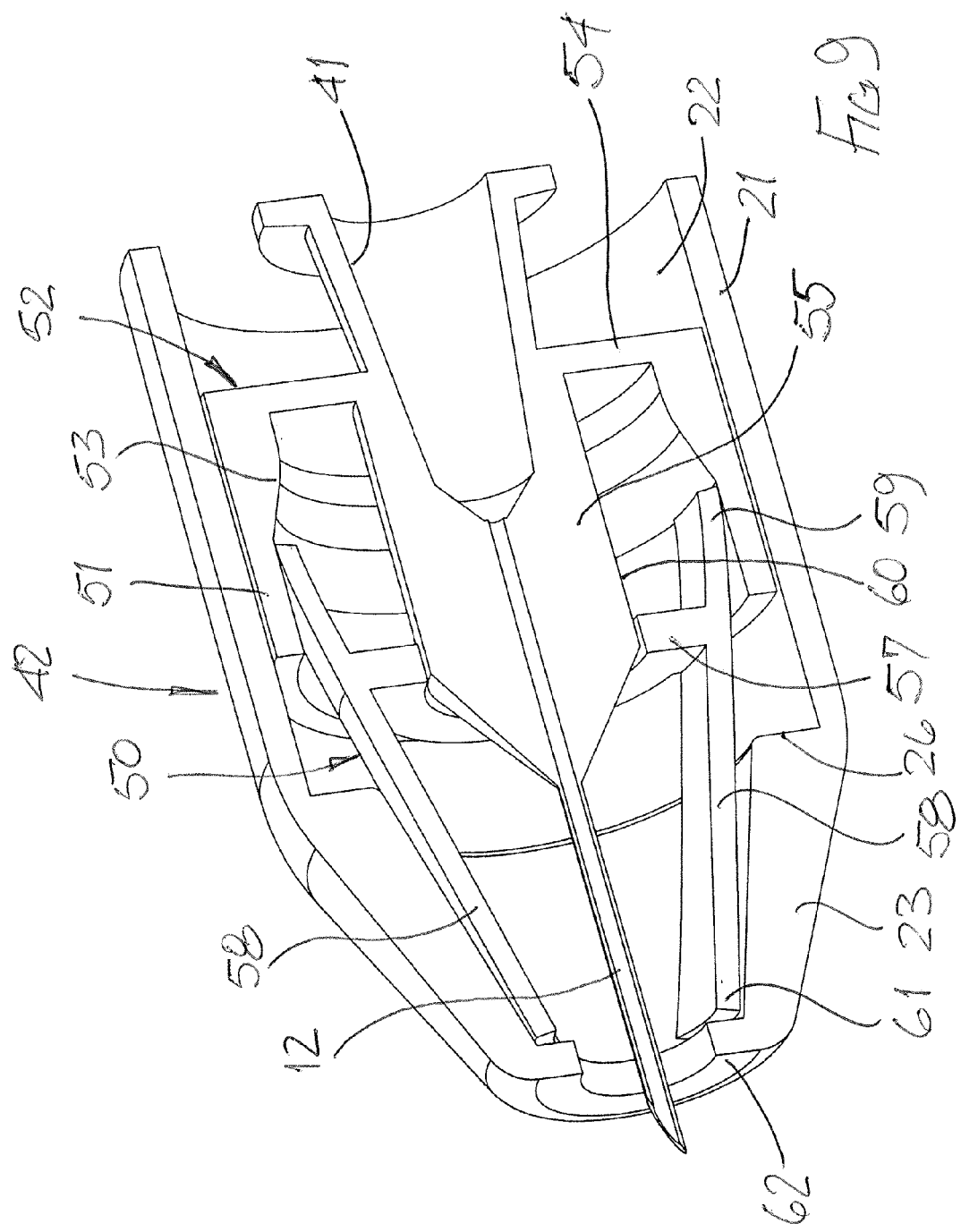
Figure 10:
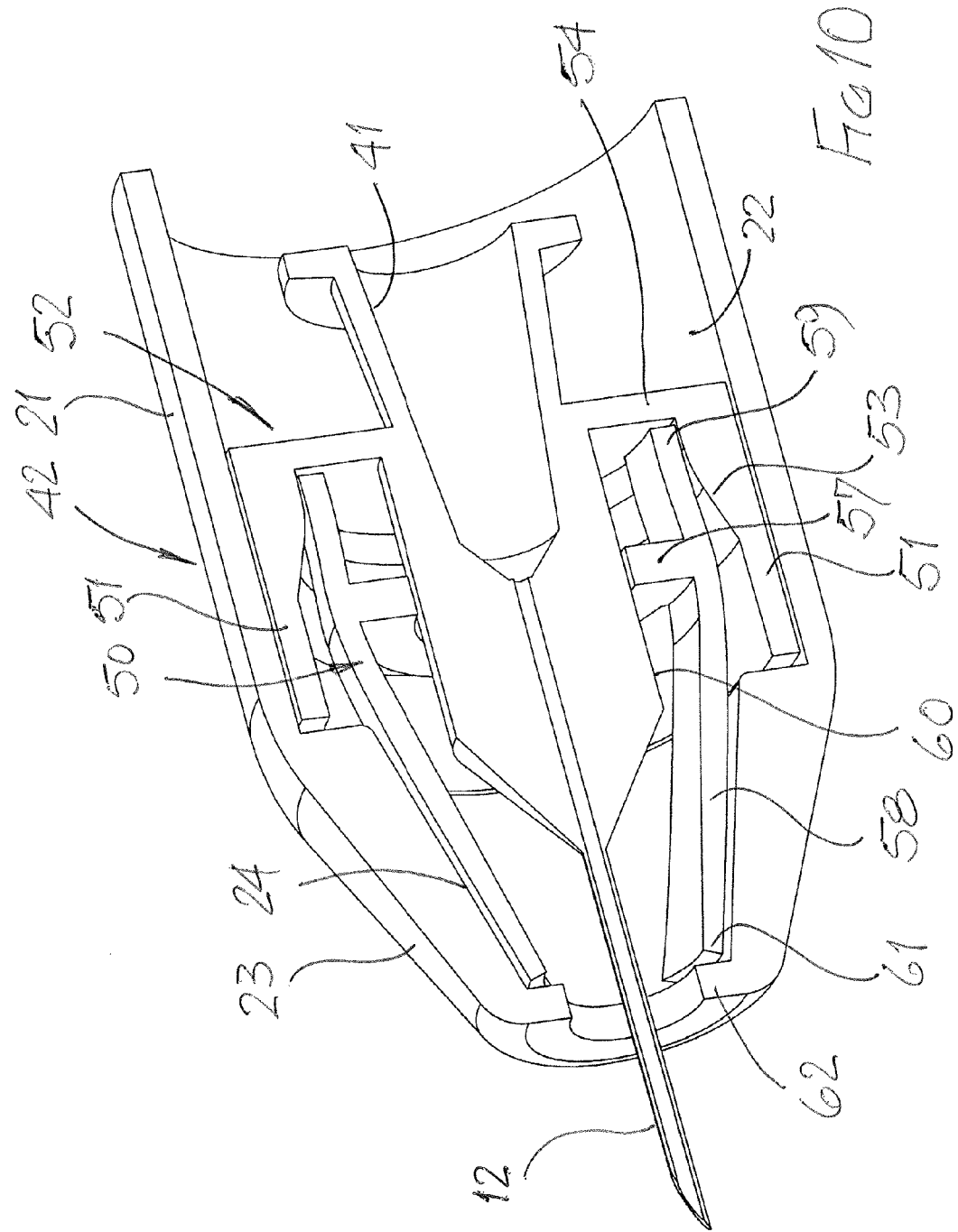

The third embodiment is shown in FIGS. 9 to 11 and again like parts, or similar parts having essentially the same function to those of FIGS. 6 to 8, are given the same reference numbers. This differs from the second embodiment in that the camming arrangement for resiliently deforming the spring and locking member 50 is formed between the rearward end of the spring and locking member and the tubular part 51 of the carrier 52. As a consequence, the spring and locking member 50 takes a somewhat different form from that of the first and second embodiments, though the sleeve 42 of this third embodiment is the same as that employed with the second embodiment.

In this third embodiment, the carrier 52 corresponds to carrier 40 of the second embodiment except that there is formed an annular cam profile 53 internally within the tubular part 51, in the region of flange 54 connecting tubular part 51 to the carrier hub 55. As with the second embodiment, the carrier has a Luer slip socket at its rearward end.

The locking member 50 has a support ring 57 carrying three equi-spaced fingers 58 each conjoined to the ring at a position approximately one quarter of the length of the finger from its rear end 59. In its initial position, the ring 57 is disposed on a parallel outer surface 60 of the hub 55, the rear ends 59 of the fingers 58 are disposed within the tubular part 51 adjacent the cam profile 53 of the tubular part 51 and the forward ends 61 of the fingers are adjacent the lip 62 at the forward end of the sleeve 42. In this position, the spring and locking member is essentially unstressed, as with the first and second embodiments.

On performing an injection, the carrier 52 moves forwardly with respect to the sleeve 42 and in view of the engagement of the forward ends 61 of the fingers with the lip 62, the rearward ends 59 of the fingers move up the cam profile 53 thereby stressing the spring and locking member 50 essentially as occurs with the first and second embodiments. Thus, the forward ends of the fingers bear on the conical internal surface of the sleeve and urge the sleeve forwardly with respect to the carrier. On completion of an injection and moving the device away from a patient, the sleeve moves forwardly under the action of the resiliently deformed fingers, until those fingers engage behind the abutment between the forward and rearward portions of the sleeve, thereby locking the sleeve in its protecting position.

In the first embodiment of FIGS. 1 to 5, the spring and locking member 30 is provided with fingers 32 disposed within sleeve 20 and arranged around the periphery of hub 11 of a carrier 10, the sleeve 20 being slidably mounted on that carrier. During forward movement of the carrier 10 from an initial position relative to the sleeve, the hub serves as a control member to perform a camming action on the fingers 32 so as resiliently to deform those fingers and increase the force between the forward ends 34 of the fingers and the tapered internal surface of the sleeve at the forward end thereof. This then applies a restorative force on the sleeve relative to the carrier so as to move the sleeve to its protecting position where it covers the needle 12 and then the forward ends of the fingers lock subsequent relative movement between the sleeve and the carrier, by engaging behind shoulder 26 on the sleeve.

The deforming of each finger so as to urge outwardly the forward end 34 thereof is performed by a camming surface 33 on the finger riding up a conical outer surface 18 serving as a control member and provided on the carrier hub 11. The spring and locking member, including the fingers, is driven rearwardly with respect to the carrier to perform this camming action by interaction between the forward end 34 of the finger and an in-turned lip 25 at the forward end of the sleeve.

Referring now to FIGS. 12A, 12B, 13 and 14 there is shown a modification of the embodiment of FIGS. 1 to 5 and insofar as is possible, like reference characters are used to designate like components or similar components having a like functionality. Such components will not be described in detail again, here. With this fourth embodiment, the carrier 65 is formed as a needle support adapted for connection to a syringe, for example, by means of a Luer slip socket 66. The hub has a conical outer surface 18, serving as a control member, at its forward end, for interaction with camming surfaces 33 on the fingers 32 of a spring and locking member 67.

With this fourth embodiment, the sleeve 20 is slidably mounted on a cylindrical outer surface 68 formed as a part of the spring and locking member 67 whereby the sleeve is indirectly supported on the carrier 65, for relative axial sliding movement with respect thereto.

Figure 12A:
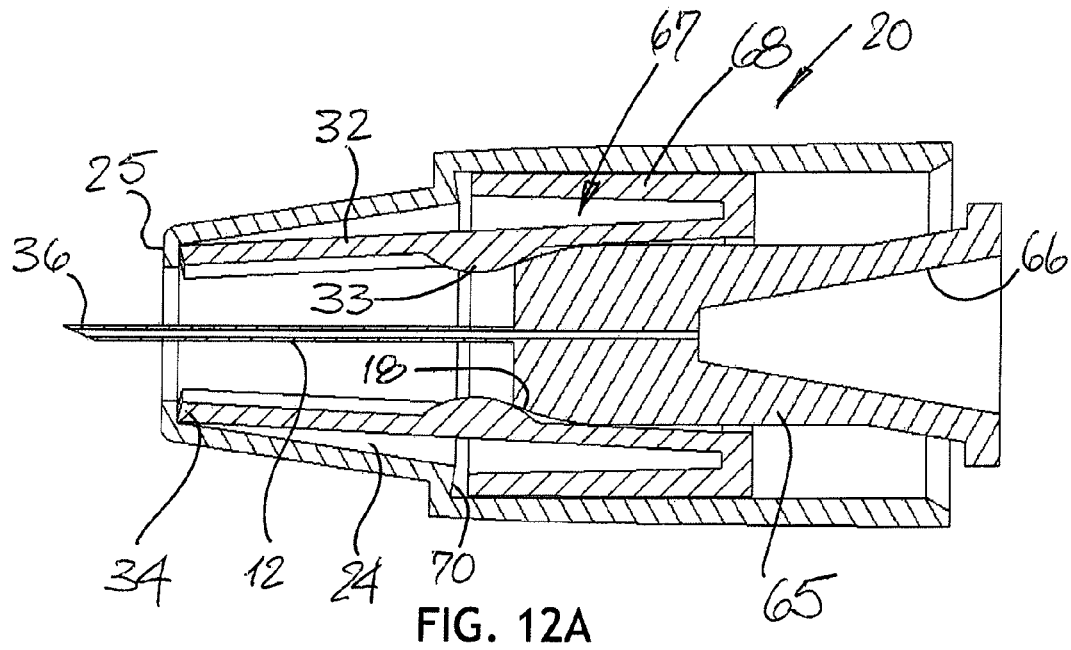
FIGS. 12A and 12B show an axial section and a cut away isometric section through a fourth embodiment when ready for use.
Figure 12B:
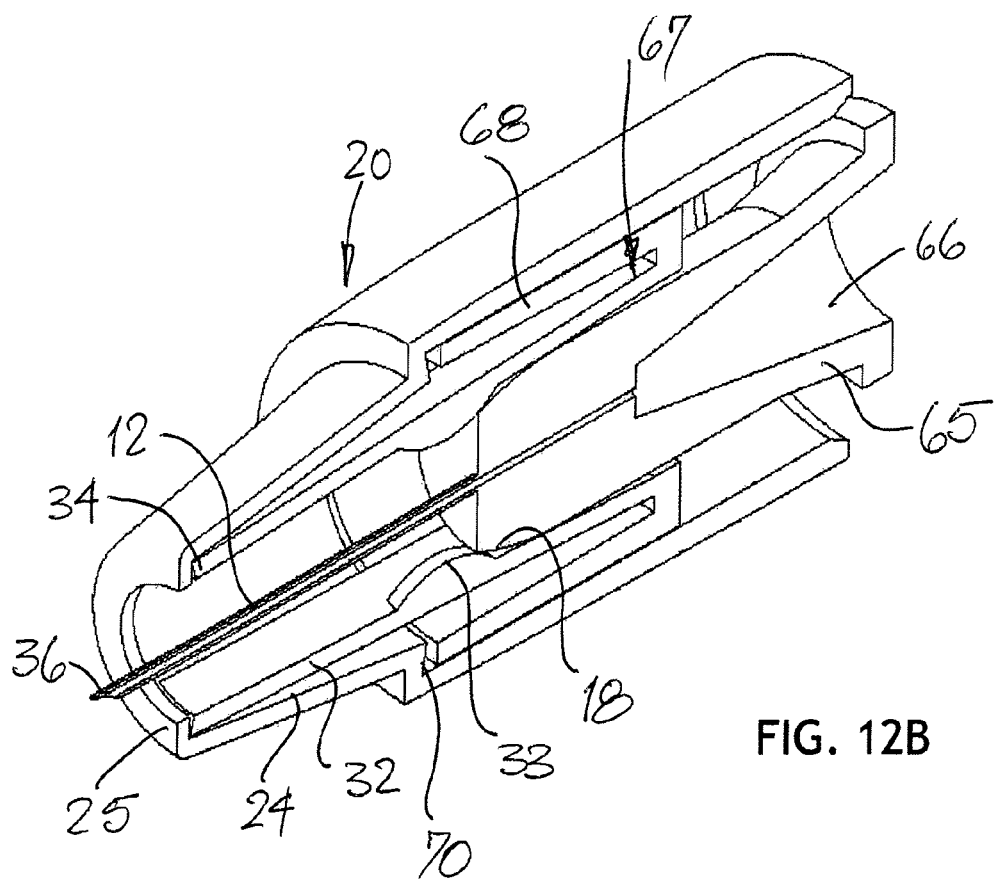

FIGS. 12A and 12B show the device in its setting ready for use. Here, the fingers 32 are wholly unstressed and so effectively in their as-moulded condition. The forward ends 34 of the fingers engage the in-turned lip 25 of the sleeve 20 and the needle tip is exposed, to allow purging of air from a connected syringe prior to the performance of an injection and also to permit viewing of the precise insertion point of the needle, when performing an injection. If required, the device could be supplied with the sleeve further forwardly with respect to the carrier 65 (and so moved to the left in FIG. 12A) so as wholly to cover the needle tip, but the sleeve would then be moved to the setting shown in FIG. 12A, prior to the performance of an injection.

Figure 13:
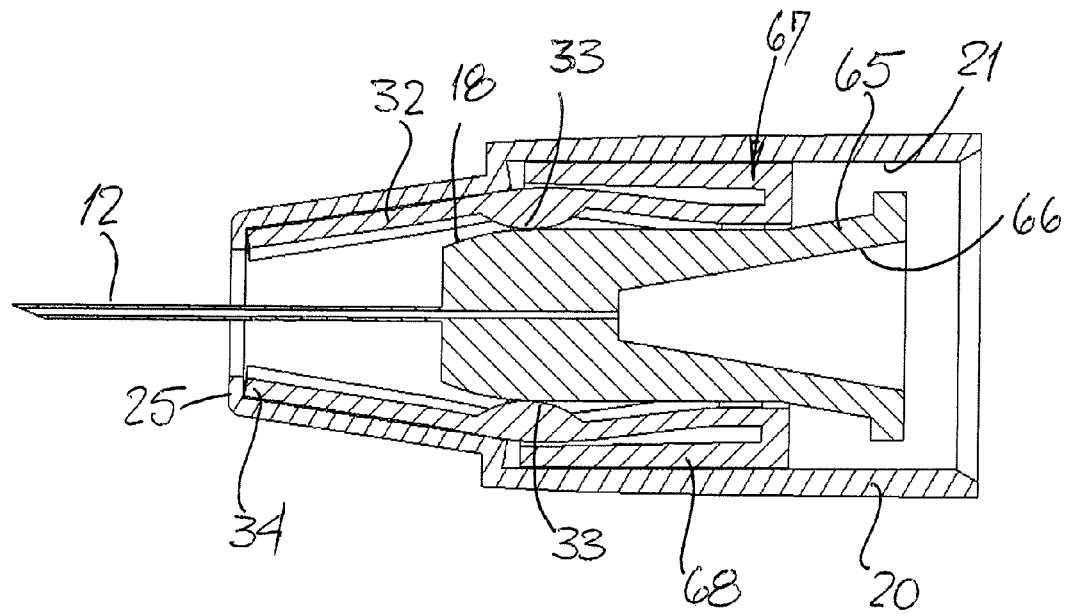
FIG. 13 is an axial section through the fourth embodiment, at the completion of an injection step.

On performing an injection, the needle carrier is pushed forwardly with respect to the sleeve 20. This causes the camming surfaces 33 to ride up the conical outer surface 18, serving as a control member, of the carrier hub, so deforming the fingers 32 into an arch shape, as shown in FIG. 13. This has the effect of increasing the force of the forward ends 34 of the fingers on the conical internal surface 24 of the forward portion of the sleeve 20, thus imparting to the sleeve a force urging the sleeve forwardly, to the left in FIG. 13.

Figure 14:
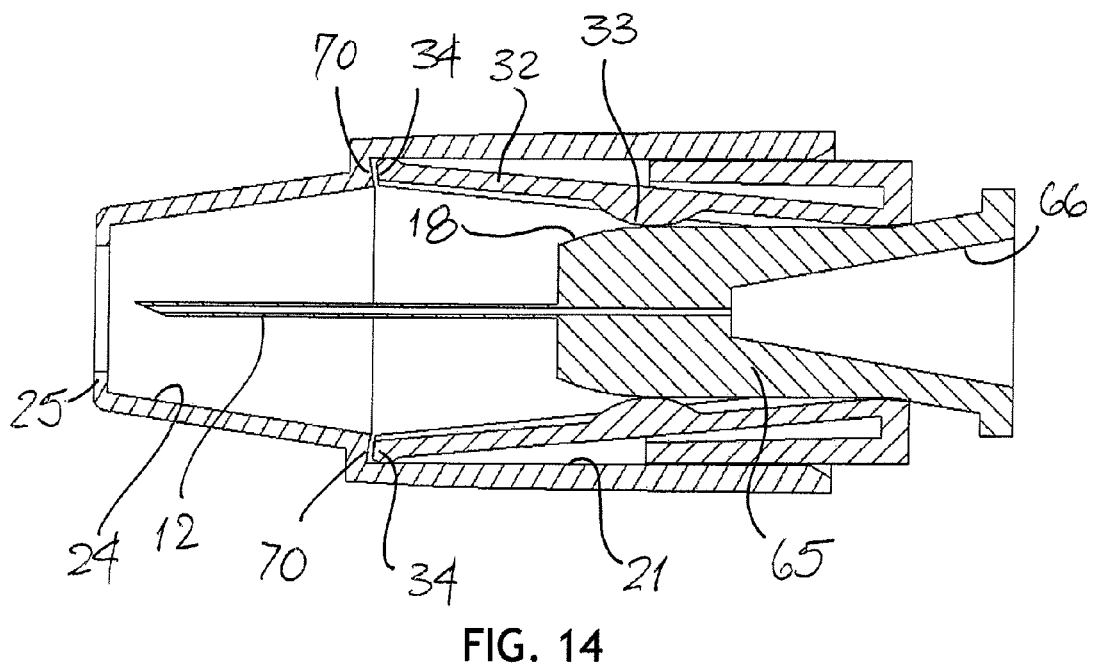
FIG. 14 is an axial section through the fourth embodiment, when the sleeve is in its protecting position after the performance of an injection.

FIG. 14 shows the device with the sleeve 20 locked in its protecting position The forward ends of the fingers, bearing in the conical internal surface 24 of the sleeve, have urged the sleeve forwardly until the forward ends have dropped off that conical internal surface and have engaged behind an annular shoulder 70, corresponding to the abutments 26 of the first embodiment. The fingers are maintained in this outward position as compared to the position shown in FIG. 12A by the interaction between the camming surfaces 33 of the fingers and the cylindrical main part of the hub, rearwardly of the conical outer surface 18.

FIGS. 15A, 15B, 16 and 17 show a fifth embodiment where the camming surfaces 33 of the fingers 32 interact with a conical surface 71 formed on a bead 72 serving as a control member and slidably supported on a forward to extension 73 of a needle carrier 74. With this embodiment, the spring and locking member comprising the fingers 32 is formed integrally with the carrier 74, which also provides a cylindrical outer surface 68 on which the sleeve 75 is slidably mounted. This sleeve differs from those of the previous embodiments in that there is provided an internal tube 76 extending rearwardly from in-turned lip 77 at the forward end thereof and engageable with the forward end of the bead 72.

Figure 15A:
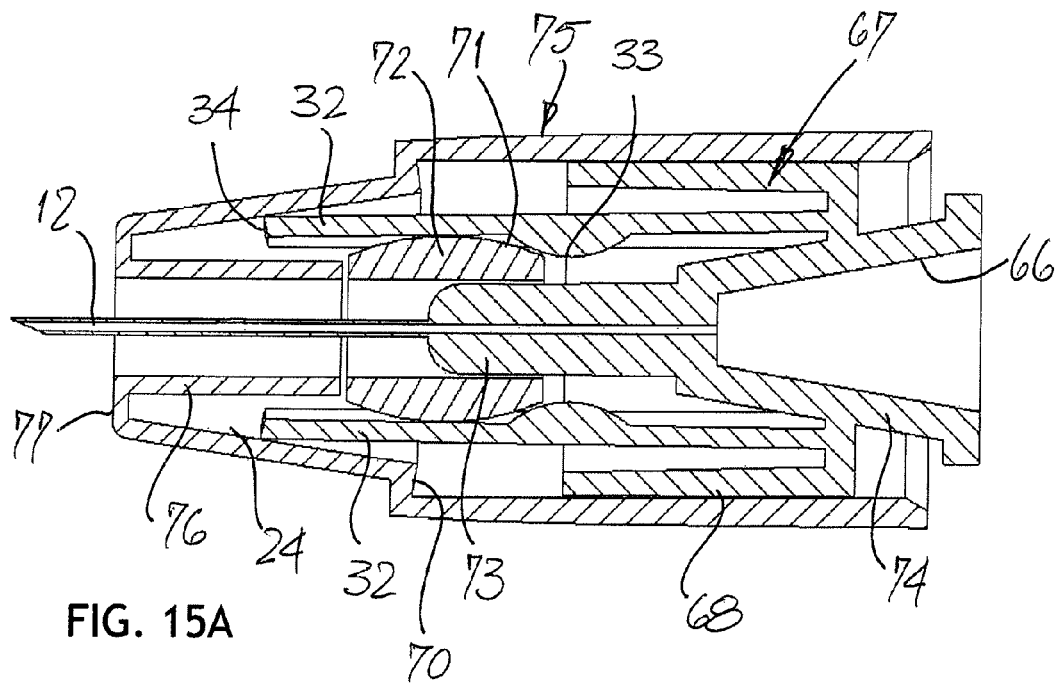
FIGS. 15A, 15B, 16 and 17 correspond to FIGS. 12A, 12B, 13 and 14 but show a fifth embodiment of the invention.
Figure 15B:
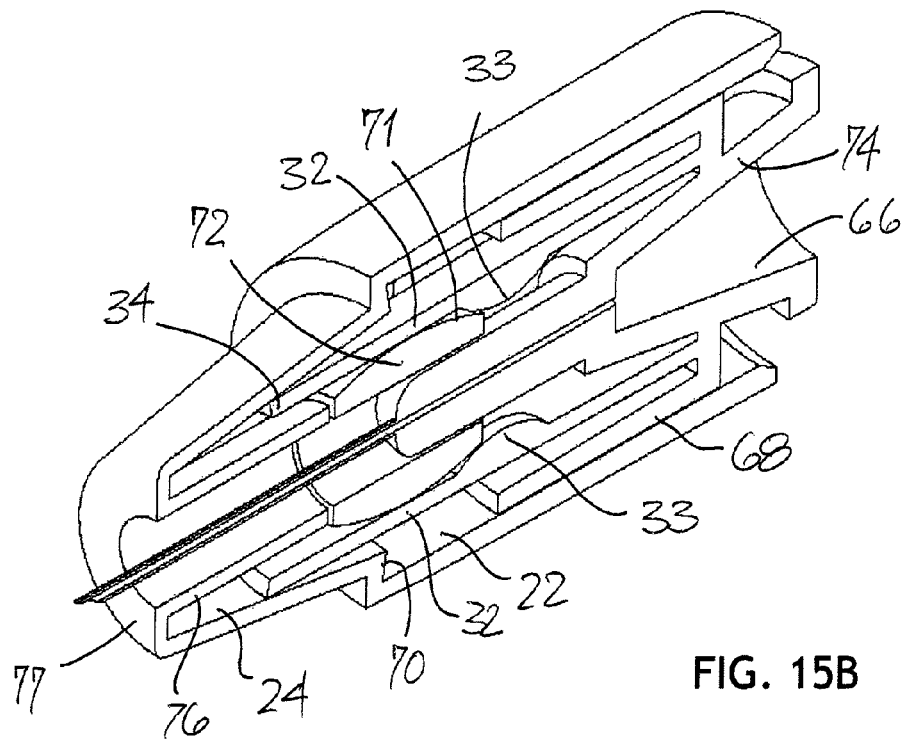

FIGS. 15A and 15B show the device in its initial position, with the bead 72 at a forward position on the extension 73 of the carrier 74 and the fingers in an unstressed as-moulded condition. The forward ends 34 of the fingers 32 lightly touch the conical internal surface 24 of the sleeve 75, partway along the length thereof.

Figure 16:
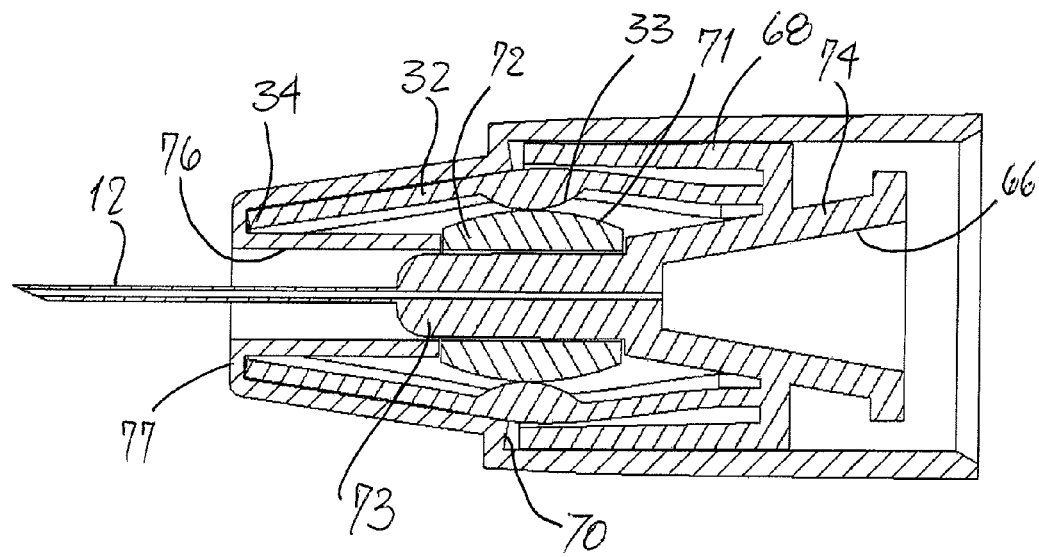

On performing an injection, the needle carrier 74 is pushed forwardly with respect to the sleeve 75. This causes the bead 72 to move rearwardly with respect to the carrier 74 and so also with respect to the fingers 32, so causing camming surfaces 33 of the fingers to ride up the conical outer surface 71 of the bead 72, so deforming the fingers 32 into an arch shape, as shown in FIG. 16. This has the effect of increasing the force of the forward ends 34 of the fingers on the conical internal surface 24 of the forward portion of the sleeve 75, thus imparting to the sleeve a force urging the sleeve forwardly, to the left in FIG. 16.

Figure 17:
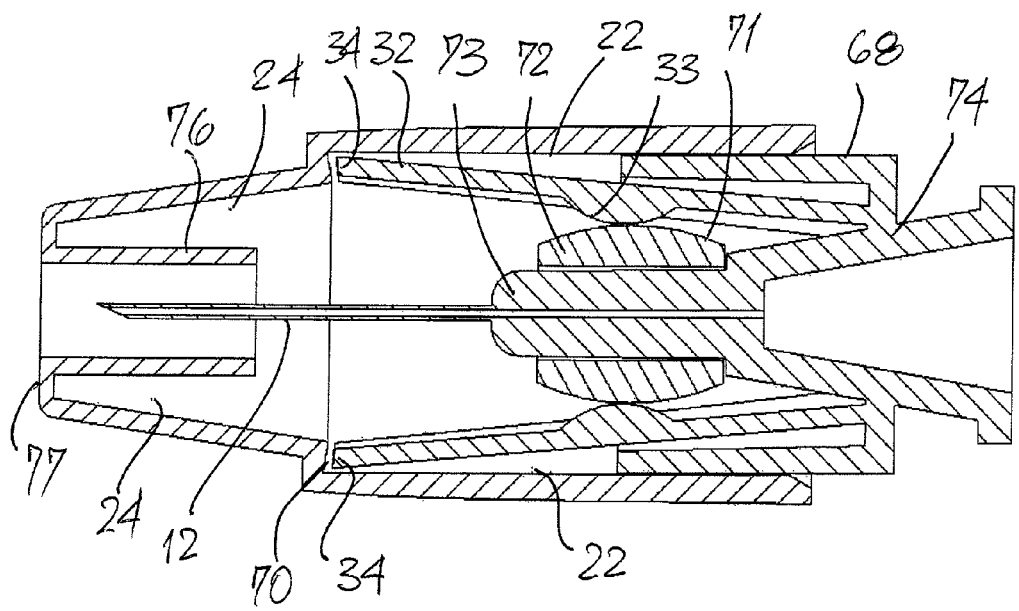

FIG. 17 shows the device with the sleeve 75 locked in its protecting position. The forward ends of the fingers, bearing in the conical internal surface 24 of the sleeve, have urged the sleeve forwardly until the forward ends have dropped off that conical internal surface and have engaged behind the annular shoulder 70. The fingers are maintained in this outward position as compared to the position shown in FIG. 15A by the interaction between the damming surfaces 33 of the fingers and the bead 72, which remains pushed rearwardly with respect to the carrier 74.

Figure 18A:
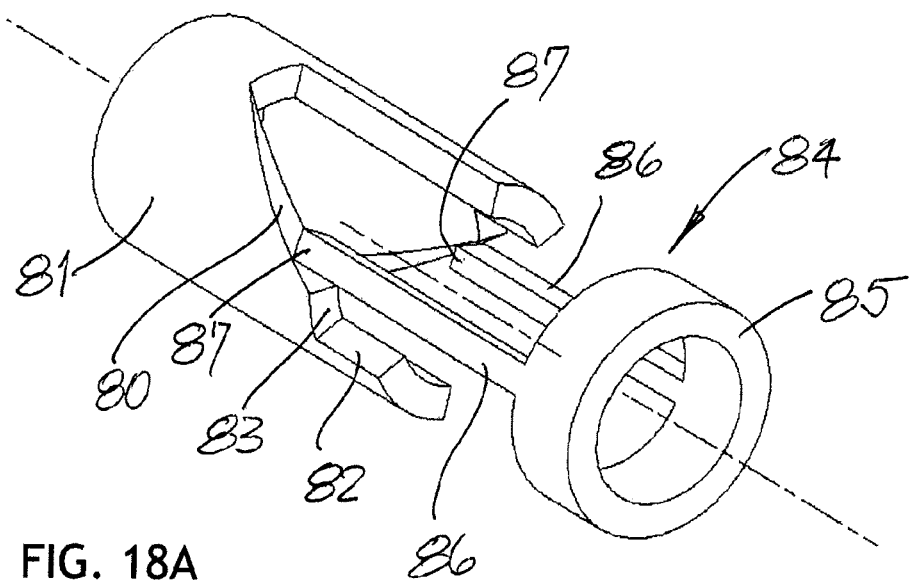
FIGS. 18A and 18B are isometric views of the operating parts of a sixth embodiment diagrammatically to illustrate the interaction of the sleeve and spring member with other components of the overall safety omitted for clarity.
Figure 18B:
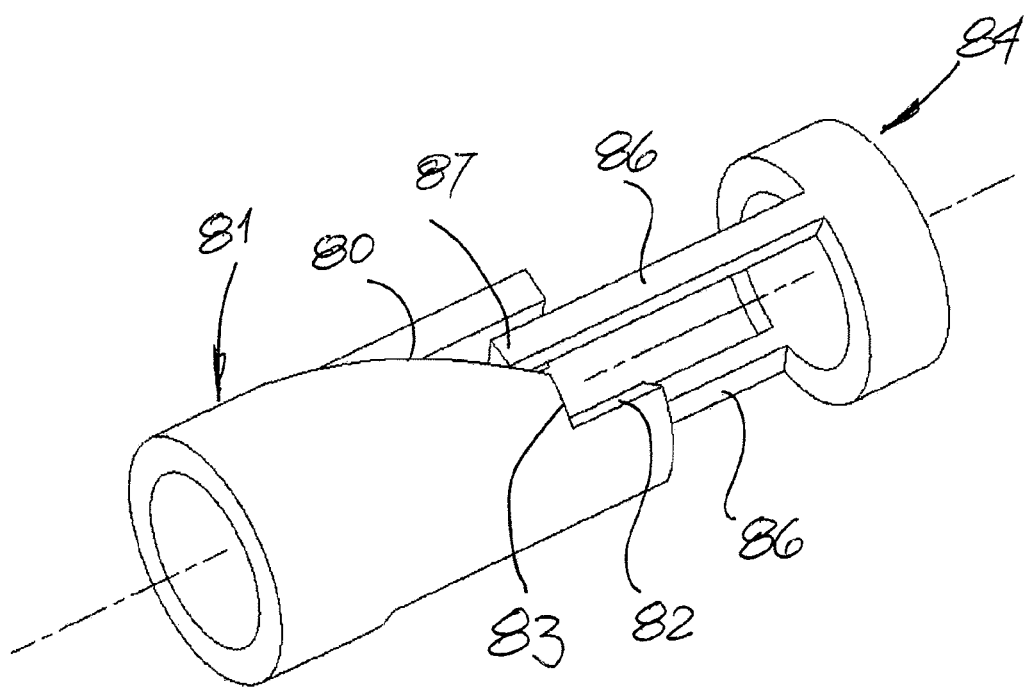
Figure 19A:
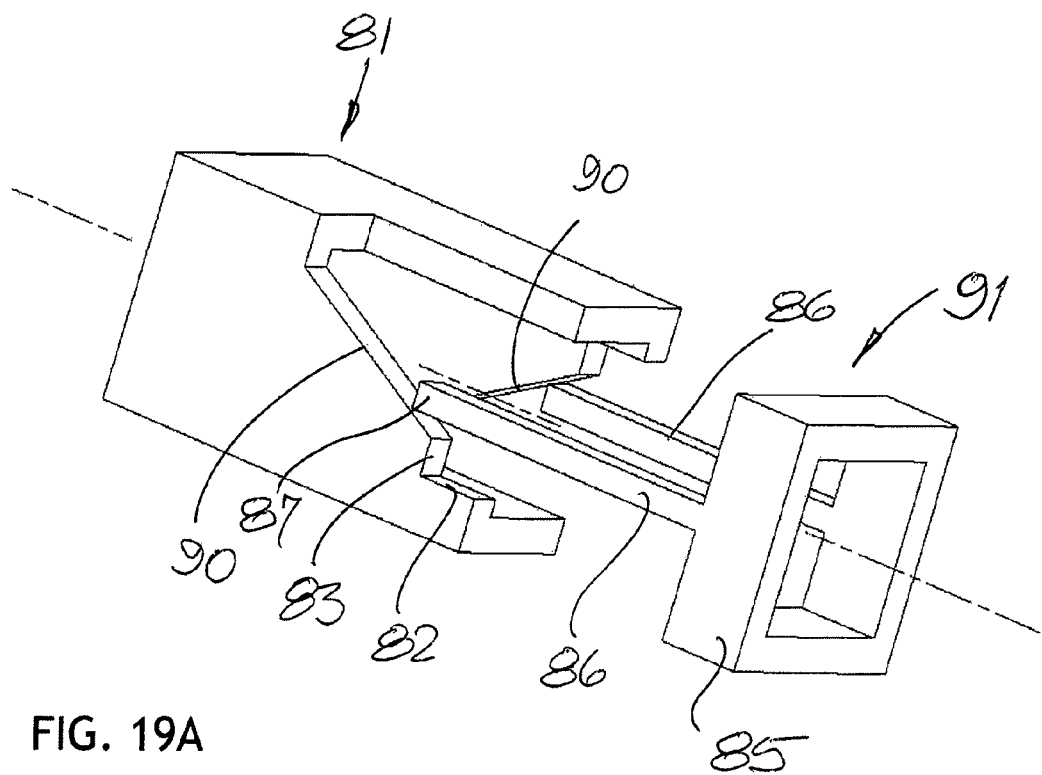
FIGS. 19A and 19B are isometric views corresponding to those of 18A and 18B but illustrating a seventh embodiment.
Figure 19B:
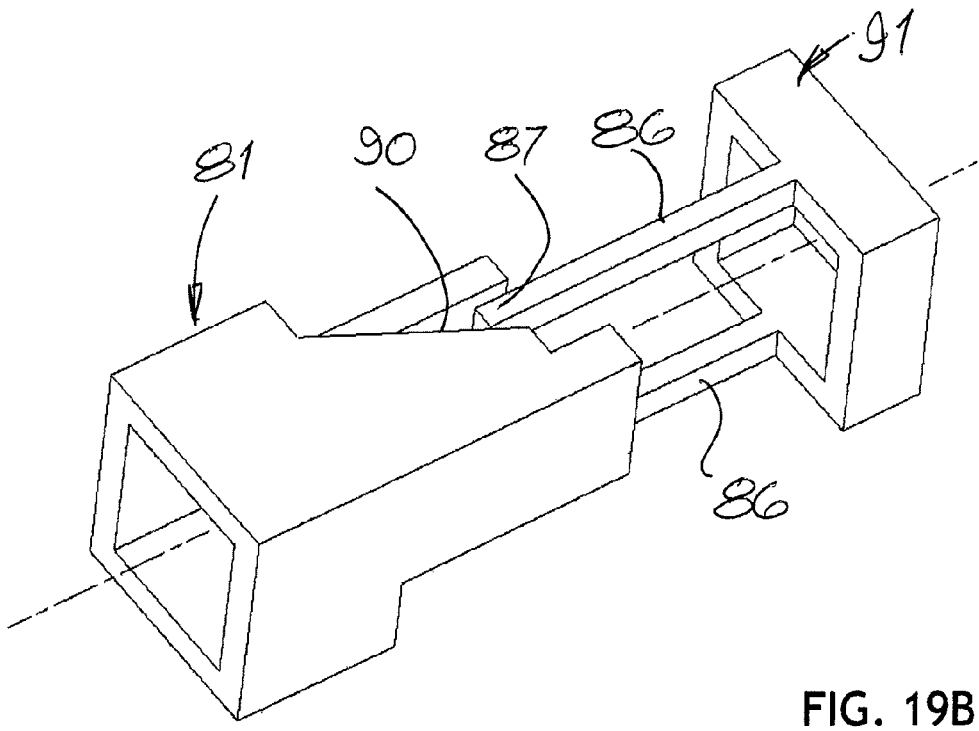

In all five embodiments described above, the fingers 32 are deformed so that the forward ends 34 thereof are urged radially outwardly to apply a resilient force to a conical surface formed as a part of a sleeve slidably mounted, either to directly or indirectly, on the needle carrier. It would however be possible to deform the fingers in a generally circumferential direction, rather than radially outwardly. FIGS. 18A and 18B show one such possibility and FIGS. 19A and 19B show a further possibility.

In the arrangement of FIGS. 18A and 18B, a pair of generally helical surfaces 80 are formed on a sleeve 81, shown only in part in these Figures. An axial surface 82 is formed rearwardly of each helical surface 80, a shoulder 83 being formed between the helical and axial surfaces.

The locking member 84 has a cylindrical base 85 from which two fingers 86 project forwardly so that the forward ends 87 thereof bear on the helical surfaces 80. FIGS. 18A and 18B show the device in its initial setting, with the fingers 86 essentially unstressed and bearing lightly on the helical surfaces 80 of the sleeve. The spring and locking member 84 is supported on the needle carrier (not shown) in much the same way as has been described above with reference to FIGS. 1 to 5 of said application but is held against relative rotation with respect to the carrier and the sleeve also is held against such relative rotation.

As with the previous embodiments, a control member (not shown, but corresponding in function for example to bead 72 of the fifth embodiment or the damming surfaces 33 and conical outer surface 18 of the first embodiment) is provided to impart a circumferential deflection to the fingers, resiliently to deform those fingers during the first stage of performing an injection.

On performing an injection, the carrier and spring and locking member 84 move forwardly with respect to the sleeve but without any relative rotation taking place, this movement causing the control member resiliently to deflect the fingers in the circumferential direction. Further axial movement drives the fingers up the helical surface 80, so resiliently deforming the fingers in the circumferential direction. The forward ends 87 of the fingers thus apply a force on the sleeve pushing the sleeve forwardly to its protecting position. Following the completion of an injection, the forward end 87 of each finger drops behind the associated shoulder 83, so locking the sleeve against further rearward movement.

FIGS. 19A and 19B show a similar arrangement but formed with components having a generally square, hollow cross-sectional shape whereby the components may be held against relative rotation. Rather than a helical surface, the sleeve is provided with a pair of oblique planar camming surfaces 90 in opposed walls of the sleeve. These camming surfaces are engaged by the forward ends 87 of the two fingers 86, provided on a locking member 91.

In other respects, the embodiment of FIGS. 19A and 19B corresponds to that of FIGS. 18A and 18B and so will not be described again, here.

Referring now to FIGS. 20A, 20B and 21 to 23 there is shown an alternative embodiment of safety device 100 intended for use with a pre-filled syringe 101 having a needle 102 permanently attached to the forward end thereof, the syringe including a plunger 103 provided with a piston 104 slidingly received within the barrel of the syringe 101. At its rearward end, the plunger 103 has an enlarged head 105 and the rearward end of the syringe barrel has an outwardly directed flange 106. Such a syringe is entirely conventional and as such, it forms no part of this invention, though it serves as the needle support in this embodiment of the invention.

The safety device 100 comprises a tubular member 108 within which the syringe 101 is received, a spring and locking member 109 and a sleeve 110 having rearward and forward portions 111 and 112 respectively. These components will now be described.

The tubular member 108 has a cylindrical outer surface 113 and an internal tubular control member 114 defining a bore within which the syringe 101 is slidably received. A pair of opposed axially extending slots 115 are formed in the outer surface of the sleeve 110, for interaction with parts of the spring and locking member 109. The forward end of the control member 114 is provided with a cam surface 116, also for interaction with the spring and locking member 109.

The spring and locking member comprises a ring-shaped base 118 from which two resiliently deformable fingers 119 project in the forward direction. Each finger has a cam 120 formed internally adjacent the base 118, for interaction with the cam surface 116 of the control member 114. Each finger has a rearward extension beyond the base, to be received in the respective slot 115 of the tubular member 108. In addition, the base 118 of the locking member 109 supports two rearwardly projecting blades 121 each of which is formed with a recess 122 for receiving the flange 106 of the syringe 101, as best seen in FIG. 20B.

The rearward portion 111 of the sleeve 110 is slidably supported on the cylindrical outer surface 113 of the tubular member 108, for movement from a rearward position shown in FIGS. 20A and 20B to a protecting position shown in FIG. 22 where the forward portion 112 of the sleeve fully surrounds the sharp tip 123 of the needle. Within the rearward portion of the sleeve, there are two rearwardly projecting pegs 124, arranged to engage the base 118 of the spring and locking member 109, with the safety device in its initial position. In this position, the tubular member 108 projects rearwardly beyond the rearward end of the sleeve 110 and the forward end of the forward portion of the sleeve is adjacent the nose of the syringe, from which the needle projects.

The forward portion of the sleeve defines two opposed internal tapering surfaces 126 for engagement by the forward ends 127 of the fingers 119. The external surface of the forward portion 112 of the sleeve is correspondingly formed, so that between the tapering surfaces, there are a pair of lands 128 against which the fingers of a user may bear in order to provide a reaction to the force given to the head 105 of the plunger 103, when performing an injection.

FIGS. 20A and 20B show the initial setting of the safety device and syringe. As can be seen, the cams 120 of the fingers 119 are immediately adjacent the cam surface 116 of the control member 114. The tubular member 108 projects rearwardly of the sleeve 110 and the flange 106 of the syringe is received in the recesses 122 of the blades 121. Further, the ring-shaped base 118 of the spring and locking member 109 bears against pegs 124. These interactions prevent relative rearward movement of the sleeve with respect to the syringe. In addition, the interaction of the rearward extensions of the fingers with the slots 115 serve to prevent the sleeve moving forwardly with respect to the spring and locking member.

An injection is performed in the conventional way. Once the needle 102 has penetrated the required injection site, an operator holds the sleeve between his index and second fingers engaged with the lands 128 whilst the thumb bears on the enlarged head 105 of the plunger to eject the drug. The head of the plunger is depressed with respect to the sleeve and so also with respect to the syringe, relative movement between the sleeve and syringe being prevented by engagement of the pegs 124 with the ring-shaped base 118 of the spring and locking member and the inter-engagement of the recesses 122 with the flange 106 of the syringe.

Towards the completion of the injection, the head 105 of the plunger 103 engages the rearward end of the tubular member 108 so that as the last of the drug is expelled from the syringe, the head of the plunger in engagement with the tubular member 108, pushes on that member 108 so that both the plunger 103 and the tubular member 108 are moved forwardly with respect to the syringe. This causes the cams 120 of the fingers 119 to ride up the cam surface 116 of the control member 114, so moving radially outwardly and resiliently deforming the fingers forwardly of the base 118. Simultaneously, this resilient deformation of the spring and locking member causes the rearward extensions of the fingers to move radially inwardly and so come clear of the slots 115, all as shown in FIG. 21. The resilient deformation of the fingers in this way causes the forward ends 127 of the fingers to bear on the tapering internal surface 126 of the sleeve, so applying a force to the sleeve which urges the sleeve to move forwardly. However, as the lands 128 of the sleeve are still engaged by the fingers of an operator, the sleeve remains in its rearward position.

On relaxing the pressure on the enlarged head 105 of the plunger 103, the entire assembly except for the sleeve moves rearwardly such that the sleeve takes up the position shown in FIG. 23, with respect to the syringe, spring and locking member and the tubular member 108. In this position, the forward ends 127 of the fingers engage a rearwardly facing shoulder 129 at the junction between the tapering internal surface 126 of the sleeve and the rearward portion 111 thereof, so locking the sleeve in this protecting position and resisting rearward movement of the sleeve with respect to the carrier and needle.

It will be appreciated that the fingers of the spring and locking member 109 are resiliently deformed so as thereafter to serve as a spring acting on the sleeve and urging the sleeve forwardly with respect to the locking member. When the safety device is in the initial position of FIGS. 20A and 20B, there is no load in the fingers 119 of the spring and locking member, and so the spring and locking member may safely and reliably be made from a plastics material. When the tubular member 108 is moved forwardly with respect to the syringe, the fingers 119 are loaded and provide a restoring force which serves to drive the sleeve 110 forwardly with respect to the syringe 101.

Further, the user may select the timing of the release of the sleeve 110 following the performance of an injection, since the device will allow relative movement between the sleeve 110 and the needle 102 to give protection to the needle only when a user releases the pressure on the head 105 of the plunger 103. However, whenever that plunger is released, the arrangement is such that the relative movement may be assured, to give protection to the used needle.

FIGS. 24A and 24B show a ninth embodiment using a similar operating principle to that described above, but intended for use with a medical needle 130 having a hub 131 formed with an internal Luer-slip connector 132 for engagement by a syringe. The hub 131 is supported within a tubular control member 133 but is free to move through a limited range of movement with respect to that member as best seen in FIG. 24A. As with the previous embodiment, the tubular member 133 has a cam surface 116 at its forward end, for interaction with cams 120 on fingers 119. Rearward movement of the carrier 113 with respect to the hub 131 is limited by the inter-engagement of the rear end of the tubular member 133 with the shoulder formed on the hub, again as shown in FIG. 24A. In other respects, this embodiment corresponds to that of FIGS. 12A, 12B, 13 and 14 of said second application and so will not be described again here.

The invention claimed is:

1. A safety device for shielding the sharp tip of a medical needle, which device comprises the following components:
    a syringe mounting a needle and having a plunger to expel a liquid drug out of the syringe through the needle;
    a sleeve for protecting the sharp tip of the needle, said sleeve being slidably mounted on the syringe and having a shielding position where the sleeve surrounds the sharp tip of the needle;
    a spring separate from the sleeve and arranged to act on the sleeve such that when sufficiently loaded the spring is able to move the sleeve to the needle shielding position; and
    a control member also separate from the sleeve and slidably movable with respect to the syringe, the control member having a camming surface arranged to interact with the spring to increase the loading thereof;
    wherein said syringe, needle, plunger, sleeve, spring and control member have respective initial positions when the device is ready for use but the spring has insufficient loading to move the sleeve to said needle shielding position, and the syringe and control member are arranged so that in the course of use of the device the plunger comes into engagement with and moves the control member relative to the spring to cause the camming surface to interact with the spring and increase the loading thereof, thereby to energize the spring sufficiently to exert a spring force on the sleeve capable of moving the sleeve to said needle shielding position.

2. A safety device as claimed in claim 1, wherein the control member projects rearwardly of the syringe, and the plunger has an enlarged head for depression by a user to perform an injection, whereby the enlarged head comes into engagement with the control member and moves the control member forwardly in the course of performing an injection.

3. A safety device as claimed in claim 2, wherein the control member is tubular and is slidably mounted on the syringe, the control member having a rearward end face for engagement by the head of the plunger.

4. A safety device as claimed in claim 3, wherein the plunger and control member are configured such that the head of the plunger comes into engagement with the control member and moves the control member forwardly towards the completion of an injection by the depression of the plunger.

5. A safety device as claimed in 1, wherein the sleeve has an open-ended rearward portion defining an essentially parallel bore and an open ended forward portion of a smaller internal size than the rearward portion and of a reducing cross-sectional area in the forward direction for at least part of the length of the forward portion, the forward portion of the sleeve when in the shielding position fully surrounding the tip of a supported needle.

6. A safety device as claimed in claim 5, wherein the part of the forward portion of a reducing cross-sectional area comprises a tapered internal surface within the forward portion.

7. A safety device as claimed in claim 6, wherein the spring comprises a leaf spring having an end portion interacting with the part of the sleeve forward portion of a reducing cross-sectional area, and the control member is arranged for relative movement with respect to the leaf spring to effect loading thereof during use of the device, the spring remaining in its loaded condition during continuing use of the device.

8. A safety device as claimed in claim 7, wherein there is a pair of leaf springs diametrically opposed about the axis of the safety device.

9. A safety device as claimed in claim 7, wherein:
the spring comprises at least one resilient finger projecting towards the second portion of the sleeve, the finger having a forward end which when in an initial setting of the spring is adjacent or contacting the internal forward surface of the sleeve with an insufficient force to cause movement of the sleeve to its needle shielding position; and
the camming surface of the control member is arranged to drive the forward end of the resilient finger away from its initial setting and urge said end of the finger towards the tapered internal surface of the sleeve sufficiently to move the sleeve to its needle shielding position on being moved by the plunger from its initial position with respect to the spring.

10. A safety device as claimed in claim 9, wherein said at least one finger of the spring has a rearward extension engaged with the sleeve to lock the sleeve against forward movement until the plunger moves the control member forwardly.

11. A safety device as claimed in claim 10, wherein movement of the control member forwardly deforms the spring so that the at least one finger of the spring is bears on the tapered internal surface of the sleeve and the rearward extension of the finger moves radially inwardly to come out of engagement with the sleeve and so release the lock thereof.

12. A safety device as claimed in claim 7, wherein there is provided a locking mechanism for the sleeve, one part of the locking mechanism being provided on the sleeve and there being a locking member interacting with said one part to lock the sleeve when in said shielding position.

13. A safety device as claimed in claim 12, wherein spring further comprises the locking member, whereby the spring and locking member both interact with said sleeve.

14. A safety device as claimed in claim 1, wherein the spring comprises a resiliently deformable spring member formed of a plastics material.

\* \* \* \* \*